US010047077B2

(12) United States Patent
Gordon

(10) Patent No.: US 10,047,077 B2
(45) Date of Patent: Aug. 14, 2018

(54) DEUTERATED O-SULFATED BETA-LACTAM HYDROXAMIC ACIDS AND DEUTERATED N-SULFATED BETA-LACTAMS

(71) Applicant: SKYLINE ANTIINFECTIVES, INC., Palo Alto, CA (US)

(72) Inventor: Eric M. Gordon, Palo Alto, CA (US)

(73) Assignee: SKYLINE ANTIINFECTIVES, INC., Palo Alto, CA (US)

( * ) Notice: Subject to any disclaimer, the term of this patent is extended or adjusted under 35 U.S.C. 154(b) by 27 days.

(21) Appl. No.: 15/486,555

(22) Filed: Apr. 13, 2017

(65) Prior Publication Data

US 2017/0298057 A1    Oct. 19, 2017

Related U.S. Application Data

(60) Provisional application No. 62/322,088, filed on Apr. 13, 2016.

(51) Int. Cl.
| | | |
|---|---|---|
| *A01N 43/00* | (2006.01) | |
| *C07D 417/12* | (2006.01) | |
| *C07B 59/00* | (2006.01) | |

(52) U.S. Cl.
CPC .......... *C07D 417/12* (2013.01); *C07B 59/002* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,710,795 A | 1/1973 | Higuch et al. | |
| 3,845,770 A | 11/1974 | Theeuwes et al. | |
| 3,916,899 A | 11/1975 | Theeuwes et al. | |
| RE28,819 E | 5/1976 | Thompson | |
| 4,008,719 A | 2/1977 | Theeuwes et al. | |
| 4,044,126 A | 8/1977 | Cook et al. | |
| 4,328,245 A | 5/1982 | Yu et al. | |
| 4,337,197 A | 6/1982 | Gordon et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu | |
| 4,414,209 A | 11/1983 | Cook et al. | |
| 4,522,811 A | 6/1985 | Eppstein et al. | |
| 4,533,660 A | 8/1985 | Gordon et al. | |
| 4,638,061 A | 1/1987 | Slusarchyk et al. | |
| 4,694,083 A | 9/1987 | Slusarchyk et al. | |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall et al. | |
| 5,120,548 A | 6/1992 | McClelland et al. | |
| 5,323,907 A | 6/1994 | Kalvelage | |
| 5,354,556 A | 10/1994 | Sparks et al. | |
| 5,591,767 A | 1/1997 | Mohr et al. | |
| 5,639,480 A | 6/1997 | Bodmer et al. | |
| 5,674,533 A | 10/1997 | Santus et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,840,674 A | 11/1998 | Yatvin et al. | |
| 5,860,957 A | 1/1999 | Jacobsen | |
| 5,891,474 A | 4/1999 | Busetti | |
| 5,900,252 A | 5/1999 | Calanchi et al. | |
| 5,922,356 A | 7/1999 | Koseki et al. | |
| 5,948,433 A | 9/1999 | Burton et al. | |
| 5,972,366 A | 10/1999 | Haynes et al. | |
| 5,972,891 A | 10/1999 | Kamei et al. | |
| 5,980,945 A | 11/1999 | Ruiz | |
| 5,983,134 A | 11/1999 | Ostrow | |
| 5,985,307 A | 11/1999 | Hanson et al. | |
| 5,985,317 A | 11/1999 | Venkateshwaran et al. | |
| 5,993,855 A | 11/1999 | Yoshimoto et al. | |
| 6,004,534 A | 11/1999 | Langer et al. | |
| 6,010,715 A | 1/2000 | Wick et al. | |
| 6,024,975 A | 2/2000 | D'angelo et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari | |

(Continued)

FOREIGN PATENT DOCUMENTS

| | | |
|---|---|---|
| EP | 0417432 | 3/1991 |
| WO | WO 2005/025506 A2 | 3/2005 |

(Continued)

OTHER PUBLICATIONS

Deuterium (Encyclopedia Britannica, retrieved from the internet Aug. 7, 2017, https://www.britannica.com/science/deuterium).*
Brittain, H., Chapter 6, pp. 205-208 in Polymorphism in Pharmaceutical Solids, (Brittain, H. ed.), Marcel Dekker, Inc. New York, (1999).
Buchwald et al., Implantable Infusion Pump Management of Insulin Resistant Diabetes Mellitus. Surgery 88:507 (1980).
Bush, K. A resurgence of -lactamase inhibitor combinations effective against multidrug-resistant Gram-negative pathogens. International J. of Antimicrobial Agents. 46:483-493 (2015).
Bush, K., et al. β-Lactams and (β-Lactamase Inhibitors: An Overview, Cold Spring Harb Perspect Med 6:a025247 (2016).
Carstensen, Jens T., Drug Stability: Principles & Practice, 2d. Ed., Marcel Dekker, NY, NY, (1995), pp. 379-380.
Clark, J.M., et al. In Vivo Evaluation of Tigemonam, a Novel Oral Monobactam. Antimicrob. Agents Chemother. 31:226-229 (1987).
Deuterium (Encyclopedia Britannica, retrieved from the internet Aug. 7, 2017, http://www.britannica.com/science/deuterium).

(Continued)

*Primary Examiner* — Daniel M Podgorski

(57) ABSTRACT

Provided herein are deuterated O-sulfated beta-lactam hydroxamic acids and deuterated N-sulfated beta-lactams, pharmaceutical compositions thereof and methods of treating infectious disease with deuterated compounds or pharmaceutical compositions thereof.

19 Claims, 5 Drawing Sheets

(56) References Cited

U.S. PATENT DOCUMENTS

| | | | |
|---|---|---|---|
| 6,113,943 A | 9/2000 | Okada et al. |
| 6,120,751 A | 9/2000 | Unger |
| 6,131,570 A | 10/2000 | Schuster |
| 6,139,865 A | 10/2000 | Friend et al. |
| 6,167,301 A | 12/2000 | Flower et al. |
| 6,197,350 B1 | 3/2001 | Yamagata et al. |
| 6,248,363 B1 | 6/2001 | Patel et al. |
| 6,256,533 B1 | 7/2001 | Yuzhakov et al. |
| 6,261,595 B1 | 7/2001 | Stanley et al. |
| 6,264,970 B1 | 7/2001 | Hata et al. |
| 6,267,981 B1 | 7/2001 | Okamoto et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 9,233,959 B2 | 1/2016 | Sommer et al. |
| 9,296,739 B2 | 3/2016 | Sommer et al. |
| 9,346,800 B2 | 5/2016 | Sommer et al. |
| 9,550,780 B2 | 1/2017 | Sommer et al. |
| 2009/0131492 A1 | 5/2009 | Hadida et al. |
| 2012/0015999 A1 | 1/2012 | Alargova et al. |
| 2012/0046330 A1 | 2/2012 | Alargova et al. |
| 2013/0116238 A1 | 5/2013 | Brand et al. |
| 2014/0128364 A1* | 5/2014 | Rodny .............. A61K 31/427 514/210.15 |
| 2015/0148326 A1 | 5/2015 | Brown et al. |

FOREIGN PATENT DOCUMENTS

| | | |
|---|---|---|
| WO | WO 2008/070619 | 6/2008 |
| WO | WO 2010/053471 | 5/2010 |
| WO | WO 2010/054138 | 5/2010 |
| WO | WO 2011/119984 | 9/2011 |
| WO | WO 2011/133751 | 10/2011 |
| WO | WO 2011/133956 | 10/2011 |
| WO | WO 2012/170061 | 12/2012 |
| WO | WO 2013/185112 | 12/2013 |
| WO | WO 2014/014841 | 1/2014 |
| WO | WO 2014/164526 | 10/2014 |
| WO | WO 2015/048370 | 4/2015 |
| WO | WO 2015/077520 | 5/2015 |
| WO | WO 2015/103583 | 7/2015 |
| WO | WO 2015/112707 | 7/2015 |
| WO | WO 2015/153877 | 10/2015 |
| WO | WO 2015/171345 | 11/2015 |
| WO | WO 2016/109361 | 7/2016 |
| WO | WO 2016/109362 | 7/2016 |
| WO | WO 2016/133989 | 8/2016 |
| WO | WO 2016/164180 | 10/2016 |
| WO | PCT/US2017/027281 | 4/2017 |

OTHER PUBLICATIONS

Fuchs, P.C., et al. In Vitro Antimicrobial Activity of Tigemonam, a New Orally Administered Monobactam. Antimicrob. Agents Chemother. 32:346-349 (1988).

Goodson, Medical Applications of Controlled Release, vol. 2, pp. 115-138 (1984).

Gordon, E.M., et al. O-Sulfated β-Lactam Hydroxamic Acids (Monosulfactams). Novel Monocyclic β-Lactam Antibiotics of Synthetic Origin. J. Am. Chem. Soc. 104(22):6053-6060.

Guillory, K., Chapter 5, pp. 202-205 in Polymorphism in Pharmaceutical Solids, (Brittain, H. ed.), Marcel Dekker, Inc., New York, NY 1999.

Hecker, et al. Discovery of a Cyclic Boronic Acid β-Lactamase Inhibitor (RPX7009) with Utility vs Class A Serine Carbapenemases. J Med Chem 58: 3682-3692 (2015).

Langer, R. New Methods of Drug Delivery. Science 249:1527-1533 (1990).

Livermore et al., Activity of OP0595/b-lactam combinations against Gram-negative bacteria with extended-spectrum, AmpC and carbapenem-hydrolysing b-lactamases. J AntiMicrob Chemother 70:3032-3041 (2015).

Sefton, M. Implantable Pumps. CRC Crit. Ref. Biomed. Eng. 14:201 (1987).

Timmins, G.S. Deuterated drugs; where are we now? Expert Opin Ther Pat. 24(10): 1067-1075 (2014).

\* cited by examiner

Synthesis of (S,Z)-2-(((1-(2-aminothiazol-4-yl)-2-((2,2-dimethyl-$d_6$-4-oxo-1-(sulfooxy)azetidin-3-yl)amino)-2-oxoethylidene)amino)oxy)acetic acid Synthesis of 2-(((Z)-(1-(2-aminothiazol-4-yl)-2-(((2R,3S)-2-$d_3$-2-methyl-4-oxo-1-(sulfooxy)azetidin-3-yl)amino)-2-oxoethylidene)amino)oxy)acetic acid.

Synthesis of 2-(((Z)-(1-(2-aminothiazol-4-yl)-2-(((2S,3S)-2-(d₃-methyl-2-methyl-4-oxo-1-(sulfooxy)azetidin-3-yl)amino)-2-oxoethylidene)amino)oxy)acetic acid.

DEUTERATED O-SULFATED BETA-LACTAM HYDROXAMIC ACIDS AND DEUTERATED N-SULFATED BETA-LACTAMS

This application claims priority under 35 U.S.C. § 119 (e) from U.S. Provisional Application Ser. No. 62/322,088, filed Apr. 13, 2016 which is hereby incorporated by reference in its entirety.

FIELD

Provided herein are deuterated O-sulfated beta-lactam hydroxamic acids and deuterated N-sulfated beta-lactams, pharmaceutical compositions thereof and methods of treating infectious disease with deuterated compounds or pharmaceutical compositions thereof.

BACKGROUND

Overuse, incorrect use and agricultural use of antibiotics has led to the emergence of resistant bacteria that are refractory to eradication by conventional anti-infective agents, such as those based on carbapenem, cephalosporin or fluoroquinolone architectures. Alarmingly, many of these resistant bacteria are responsible for common infections including, for example, pneumonia, sepsis, etc.

The dearth of new antibiotic agents, which, inter alia, is due to termination of research and development efforts to develop new antibiotics agents, has exacerbated the above situation. Even at this date, when a clear need for novel antibiotic agents has been established, reduced economic incentives and heightened regulatory requirements has prevented substantial investment by pharmaceutical organizations in this increasingly critical issue in health care.

Failure to provide new agents to treat resistant bacteria threatens the many benefits achieved with antibiotics in the recent past. Accordingly, what is need are novel antibiotic compounds which are effective against resistant bacteria and are simple to manufacture and use.

SUMMARY

The present application satisfies these and other needs by providing deuterated O-sulfated beta-lactam hydroxamic acids and deuterated N-sulfated beta-lactams, which may be used to treat infectious diseases. In one aspect, tigemonam or aztreonam, where any or up to all of the non-exchangeable hydrogen atoms are substituted with deuterium are provided.

In another aspect, a compound of structural Formula (I) is provided:

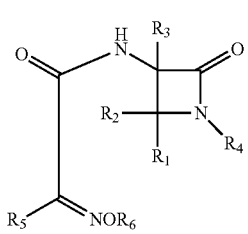

(I)

and pharmaceutically acceptable salts, hydrates and solvates thereof, where $R_1$ and $R_2$ are independently hydrogen, deuterium, —$CH_3$, —$CD_3$, —$CD_2H$ or —$CDH_2$, $R_3$ is hydrogen or deuterium, $R_4$ is —$SO_3H$ or —$OSO_3H$, $R_5$ is heteroaryl or substituted heteroaryl optionally substituted with one or more deuterium atoms; and $R_6$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or —$CO_2H$, optionally substituted with one or more deuterium atoms, provided that at least one non-exchangeable hydrogen atom is substituted with deuterium.

Also provided are derivatives, including esters, enol ethers, enol esters, metabolites and prodrugs of the compounds described herein. Further provided are pharmaceutical compositions which include the compounds provided herein and a pharmaceutically acceptable vehicle.

Methods of treating, preventing, or ameliorating symptoms of infectious disease in a subject are also presented herein. The methods generally involve administering a therapeutically effective amount of deuterated O-sulfated beta-lactam hydroxamic acids and/or deuterated N-sulfated beta-lactams, or pharmaceutical compositions thereof to the subject.

DETAILED DESCRIPTION

Definitions

Figure 1:
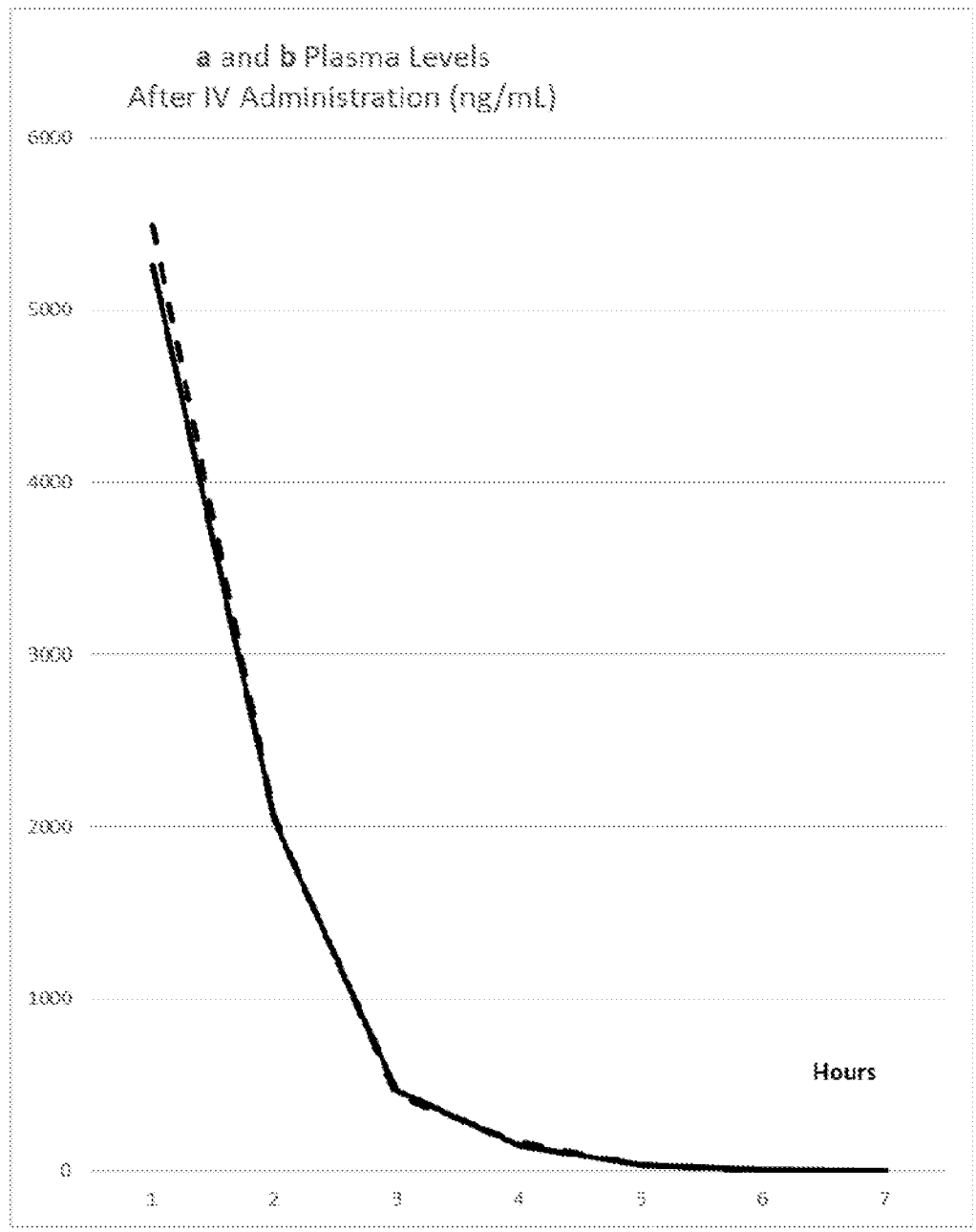
FIG. 1 is a graph which illustrates IV dosing of tigemonam (solid line) and (S,Z)-2-(((1-(2-aminothiazol-4-yl)-2-((2,2-dimethyl-$d_6$-4-oxo-1-(sulfooxy)azetidin-3-yl)amino)-2-oxoethylidene)amino)oxy)acetic acid (dashed line) in rats where the y axis is plasma concentration (ng/mL) and the x axis is time (hours).

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en- 1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Aryl" by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl" by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds described herein include, but are not limited to, $^2$H, $^3$H, $^{13}$C, $^{14}$C, $^{15}$N, $^{18}$O, $^{17}$O, $^{35}$S, etc. In general, it should be understood that all isotopes of any of the elements comprising the compounds described herein may be found in these compounds. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present application. Further, it should be understood, when partial structures of the compounds are illustrated, that brackets indicate the point of attachment of the partial structure to the rest of the molecule.

"Deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

"Is/are deuterium," when used to describe a given position in a molecule such as $R_1$-$R_{30}$ or the symbol "D", when used to represent a given position in a drawing of a molecular structure, means that the specified position is enriched with deuterium above the naturally occurring distribution of deuterium. The same is true of the term "contains deuterium," which is often used to refer to methyl groups which may be mono-, di- or trideuterated (e.g., such groups may be —$CH_2D$, —$CD_2H$, and —$CD_3$, wherein each position denoted D is enriched with deuterium above the naturally occurring distribution of deuterium). In some embodiments deuterium enrichment is no less than about 1%, in others no less than about 5%, in others no less than about 10%, in another no less than about 20%, in another no less than about 50%, in others no less than about 70%, in others no less than about 80%, in others no less than about 90%, or in others no less than about 98% of deuterium at the specified position.

"Heteroalkyl," "Heteroalkanyl," "Heteroalkenyl" and "Heteroalkynyl" by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$—, =N—N=, —N=N—, —N=N—NR$^{503}$R$^{504}$, —PR$^{505}$—, —P(O)$_2$—, —POR$^{506}$—, —O—P(O)$_2$—, —SO—, —SO$_2$—, —SnR$^{507}$R$^{508}$— and the like, where R$^{501}$, R$^{502}$, R$^{503}$, R$^{504}$, R$^{505}$, R$^{506}$, R$^{507}$ and R$^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or spa carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202-205 in *Polymorphism in Pharmaceutical Solids*, (Brittain, H. ed.), Marcel Dekker, Inc., New York, N.Y., 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by taking the compound in a preventative fashion. The application of a therapeutic for preventing or prevention of a disease of disorder is known as 'prophylaxis.' In some embodiments, the compounds provided herein provide superior prophylaxis because of lower long term side effects over long time periods.

"Prodrug" refers to a derivative of a drug molecule that requires a transformation within the body to release the active drug. Prodrugs are frequently (though not necessarily) pharmacologically inactive until converted to the parent drug.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In some embodiments, the salt is pharmaceutically acceptable.

"Solvates" refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205-208 in *Polymorphism in Pharmaceutical Solids*, (Brittain, H. ed.), Marcel Dekker, Inc., New York, N.Y., 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-ray diffraction, X-ray powder diffraction, Polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205-208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted" when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each W is independently $R^b$ or alternatively, the two $R^c$'s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art. The substituents used to substitute a specified group can be further substituted, typically with one or more of the same or different groups selected from the various groups specified above. In some embodiments, substituents are limited to the groups above.

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. Treatment can also refer to the lessening of the severity and/or the duration of one or more symptoms of a disease or disorder. In a further feature, the treatment rendered has lower potential for long term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject. In some embodiments, the vehicle is pharmaceutically acceptable.

It should be noted that there are alternative ways of implementing the present invention. Accordingly, the present embodiments are to be considered as illustrative and not restrictive, and the invention is not to be limited to the details given herein, but may be modified within the scope and equivalents of the appended claims.

Compounds

Provided herein are deuterated O-sulfated beta-lactam hydroxamic acids and deuterated N-sulfated beta-lactams, which may be used to treat infectious diseases. Deuteration of O-sulfated beta-lactam hydroxamic acids and N-sulfated beta-lactams, may, in some instances, increase the anti-infective activity and/or alter important pharmacological properties, such as, for example, toxicity, clearance, blood levels or bioavailability of the compounds described herein in a beneficial manner.

In some embodiments, a compound of structural Formula (I) is provided:

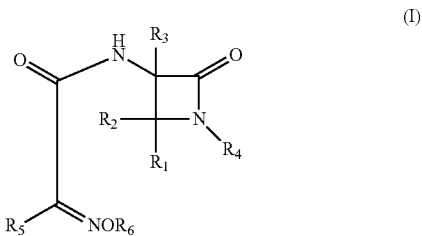

(I)

or pharmaceutically acceptable salts, hydrates, solvates and polymorphs thereof, where $R_1$ and $R_2$ are independently hydrogen, deuterium, —$CH_3$, —$CD_3$, —$CD_2H$ or —$CDH_2$, $R_3$ is hydrogen or deuterium, $R_4$ is —$SO_3H$ or —$OSO_3H$, $R_5$ is heteroaryl or substituted heteroaryl optionally substituted with one or more deuterium atoms; and $R_6$ is alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or —$CO_2H$, optionally substituted with one or more deuterium atoms, provided that at least one non-exchangeable hydrogen atom is substituted with deuterium.

In certain embodiments are provided compounds as disclosed herein, wherein at least one of $R_1$-$R_{30}$ independently has deuterium enrichment of no less than about 1%. In certain embodiments are provided compounds as disclosed herein, wherein at least one of $R_1$-$R_{30}$ independently has deuterium enrichment of no less than about 10%. In certain embodiments are provided compounds as disclosed herein, wherein at least one of $R_1$-$R_{30}$ independently has deuterium enrichment of no less than about 50%. In certain embodiments are provided compounds as disclosed herein, wherein at least one of $R_1$-$R_{30}$ independently has deuterium enrichment of no less than about 90%. In certain embodiments are provided compounds as disclosed herein, wherein at least one of $R_1$-$R_{30}$ independently has deuterium enrichment of no less than about 95%. In certain embodiments are provided compounds as disclosed herein, wherein at least one of $R_1$-$R_{30}$ independently has deuterium enrichment of no less than about 98%.

In certain embodiments are provided compounds as disclosed herein wherein each position represented as D has deuterium enrichment of no less than about 1%. In certain embodiments are provided compounds as disclosed herein wherein each position represented as D has deuterium enrichment of no less than about 10%. in certain embodiments are provided compounds as disclosed herein wherein each position represented as D has deuterium enrichment of no less than about 50%. In certain embodiments are provided compounds as disclosed herein wherein each position represented as D has deuterium enrichment of no less than about 90%. In certain embodiments are provided compounds as disclosed herein wherein each position represented as D has deuterium enrichment of no less than about 95%. In certain embodiments are provided compounds as disclosed herein wherein each position represented as D has deuterium enrichment of no less than about 98%.

In certain embodiments, the deuterated compounds disclosed herein maintain the beneficial aspects of the corresponding non-isotopically enriched molecules, while substantially increasing the maximum tolerated dose, increasing bioavailability, increasing blood levels, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions. In particular embodiments, the deuterated compounds disclosed herein maintain the beneficial aspects of the corresponding non-isotopically enriched molecules, while substantially increasing oral bioavailability.

In some embodiments, if $R_1$ and $R_2$ are both —$CH_3$, then either $R_3$ is deuterium or $R_5$ or $R_6$ is substituted with at least one deuterium. In other embodiments, if $R_1$ or $R_2$ is hydrogen or deuterium then the other of $R_1$ or $R_2$ is not hydrogen or deuterium. In still other embodiments, if $R_1$ or $R_2$ are independently hydrogen or —$CH_3$, then either $R_3$ is deuterium or $R_5$ or $R_6$ is substituted with at least one deuterium. In still other embodiments, $R_1$ and $R_2$ are not both —$CH_3$. In still other embodiments, $R_1$ and $R_2$ are not independently both hydrogen or —$CH_3$. In still other embodiments, $R_6$ is alkyl, substituted alkyl, aryl, substituted aryl, arylalkyl, substituted arylalkyl, heteroalkyl, substituted heteroalkyl or —$CO_2H$.

In any of the above embodiments, $R_5$ is

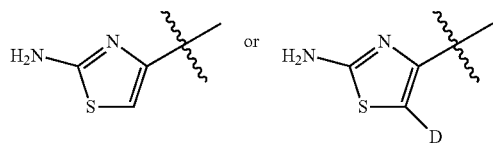 [SMILES: *c1csc(N)n1 ; *c1nc(N)sc1[2H]]

and $R_6$ is selected from the fragments listed in Table 1, below, where the crossed line is the point of attachment of $R_6$ to the oxime oxygen.

In some embodiments, $R_1$ and $R_2$ are $CD_3$, $R_3$ is H, $R_4$ is —$OSO_3H$, $R_5$ is

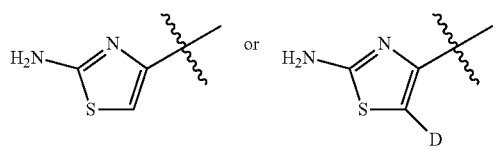 [SMILES: *c1csc(N)n1 ; *c1nc(N)sc1[2H]]

and $R_6$ is selected from the fragments listed in Table 1, below, where the crossed line is the point of attachment of $R_6$ to the oxime oxygen.

In some embodiments, $R_1$ is $CD_3$, $R_2$ and $R_3$ are H, $R_4$ is —$SO_3H$, $R_5$ is

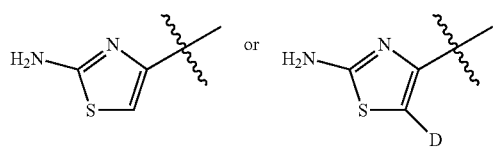 [SMILES: *c1csc(N)n1 ; *c1nc(N)sc1[2H]]

and $R_6$ is selected from the fragments listed in Table 1, below, where the crossed line is the point of attachment of $R_6$ to the oxime oxygen.

TABLE 1

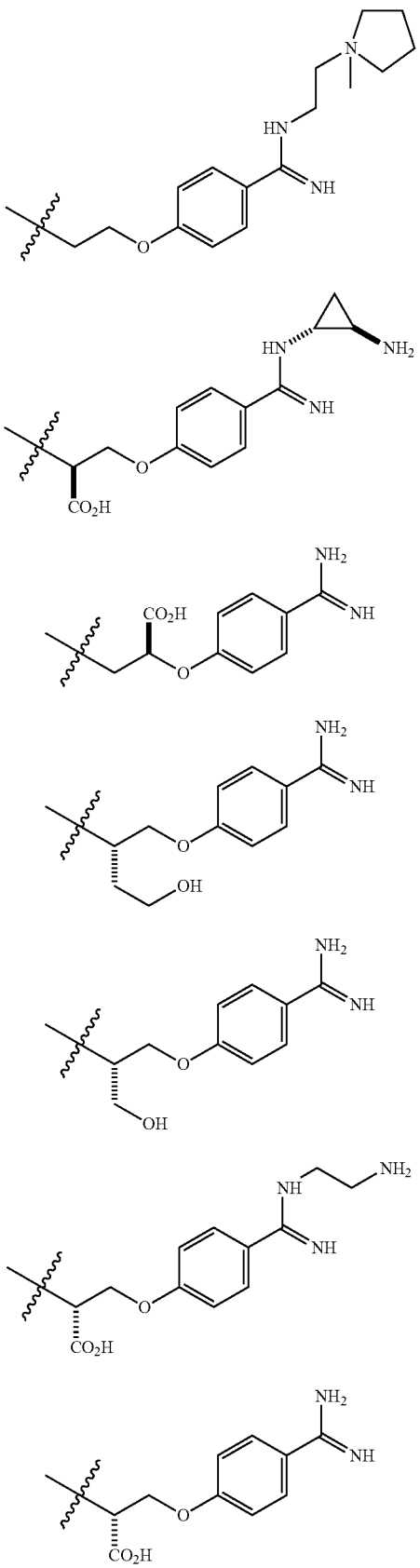

TABLE 1-continued
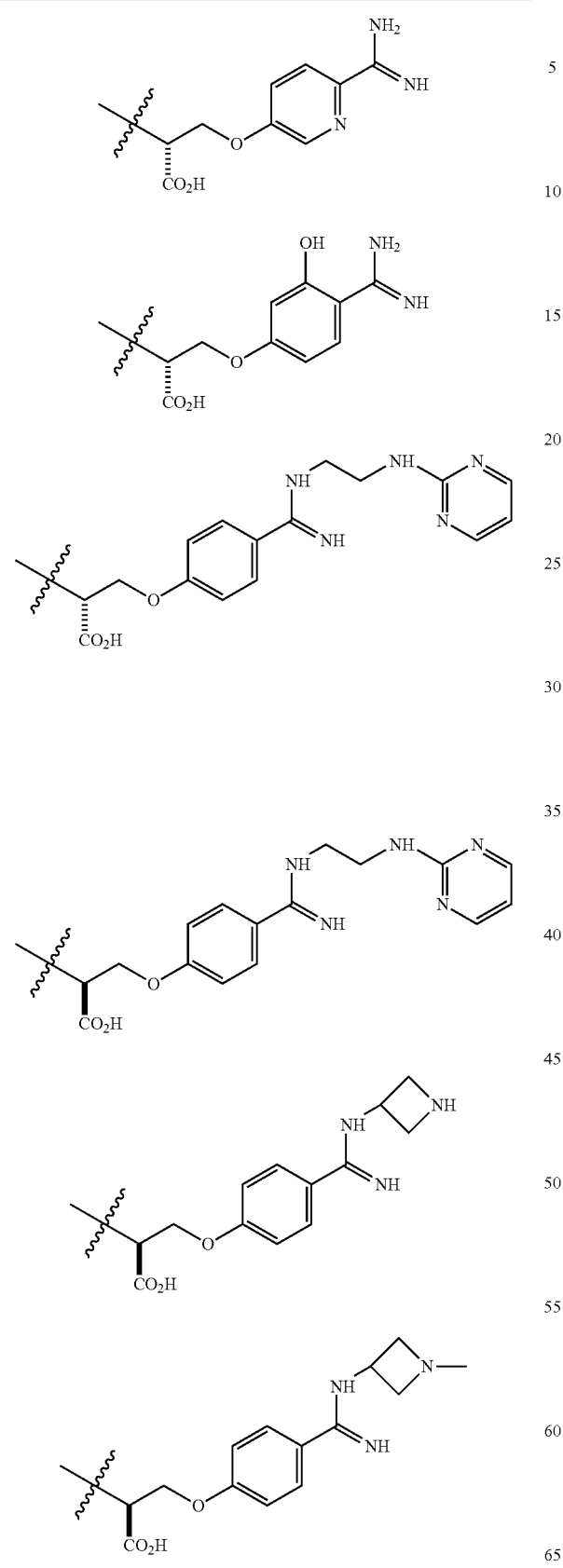
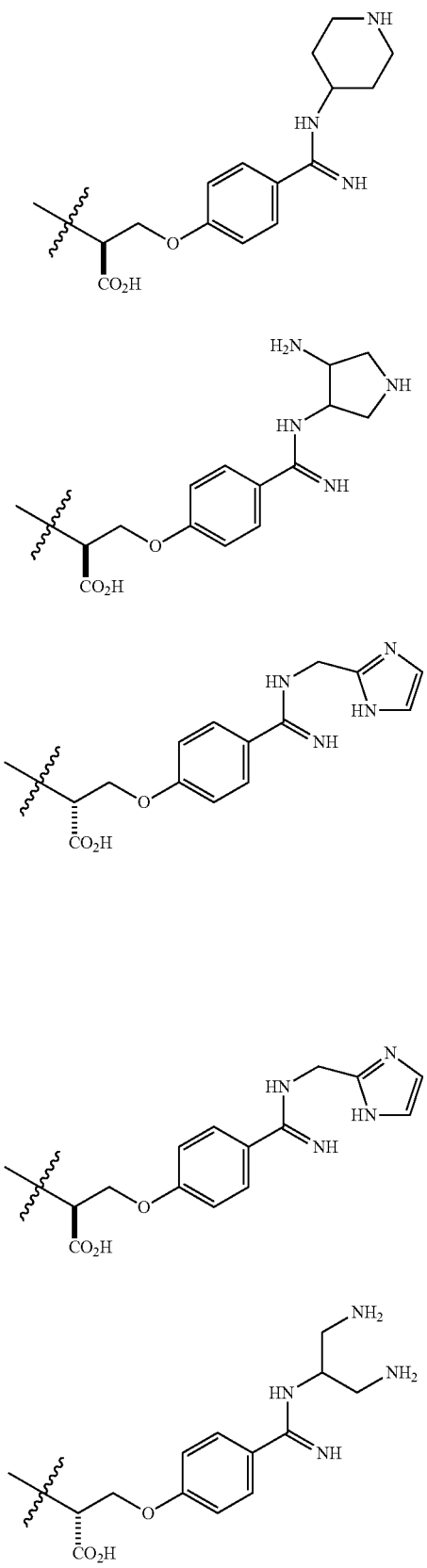

TABLE 1-continued
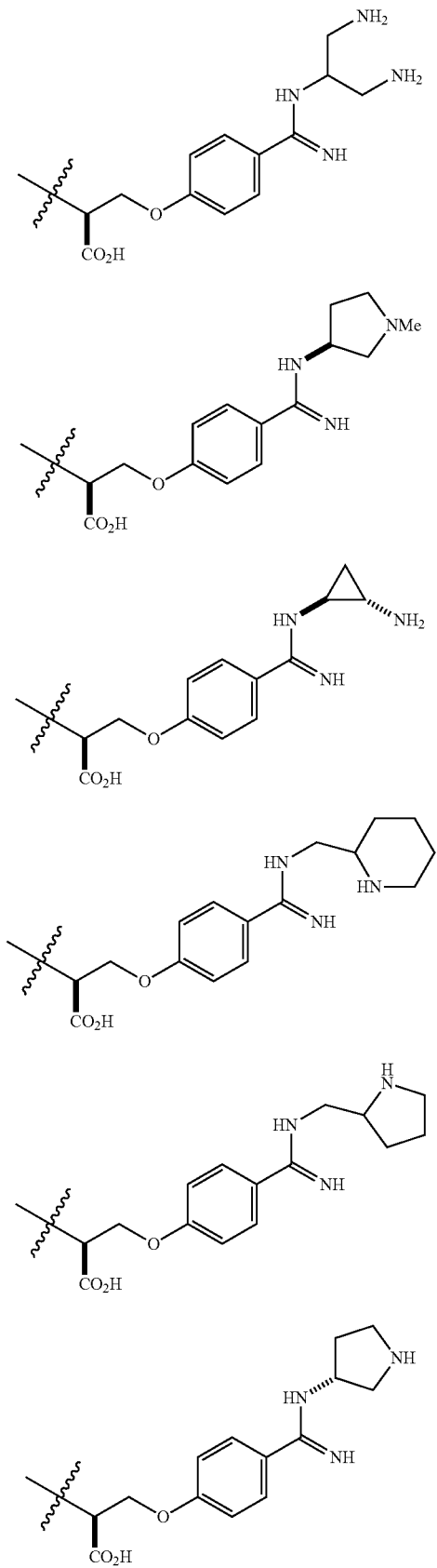
TABLE 1-continued
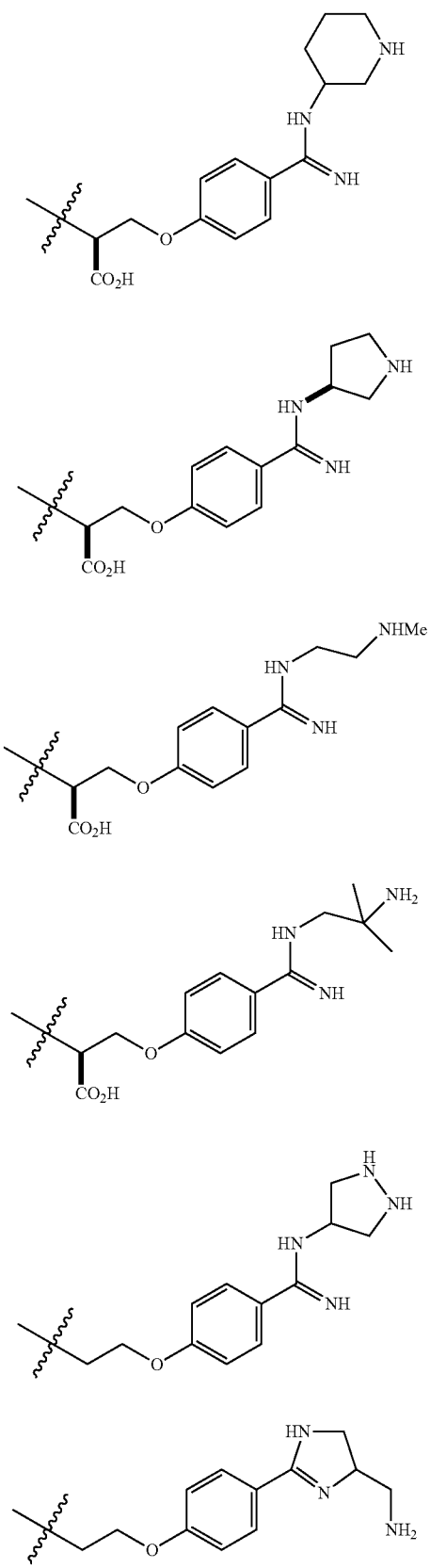

TABLE 1-continued
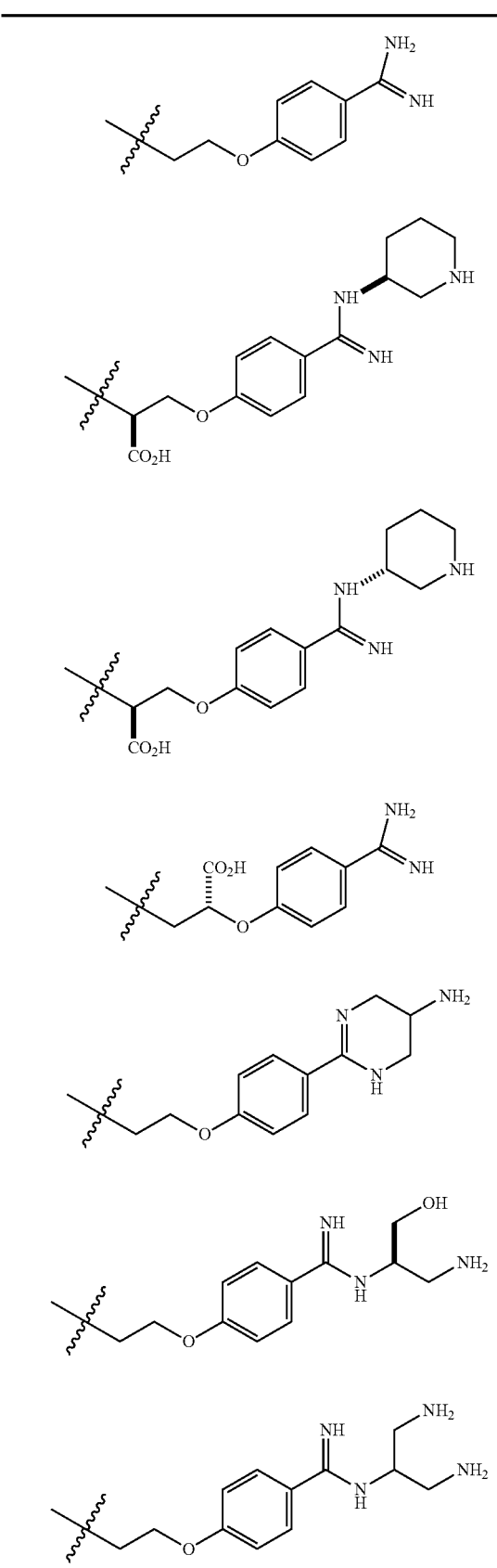
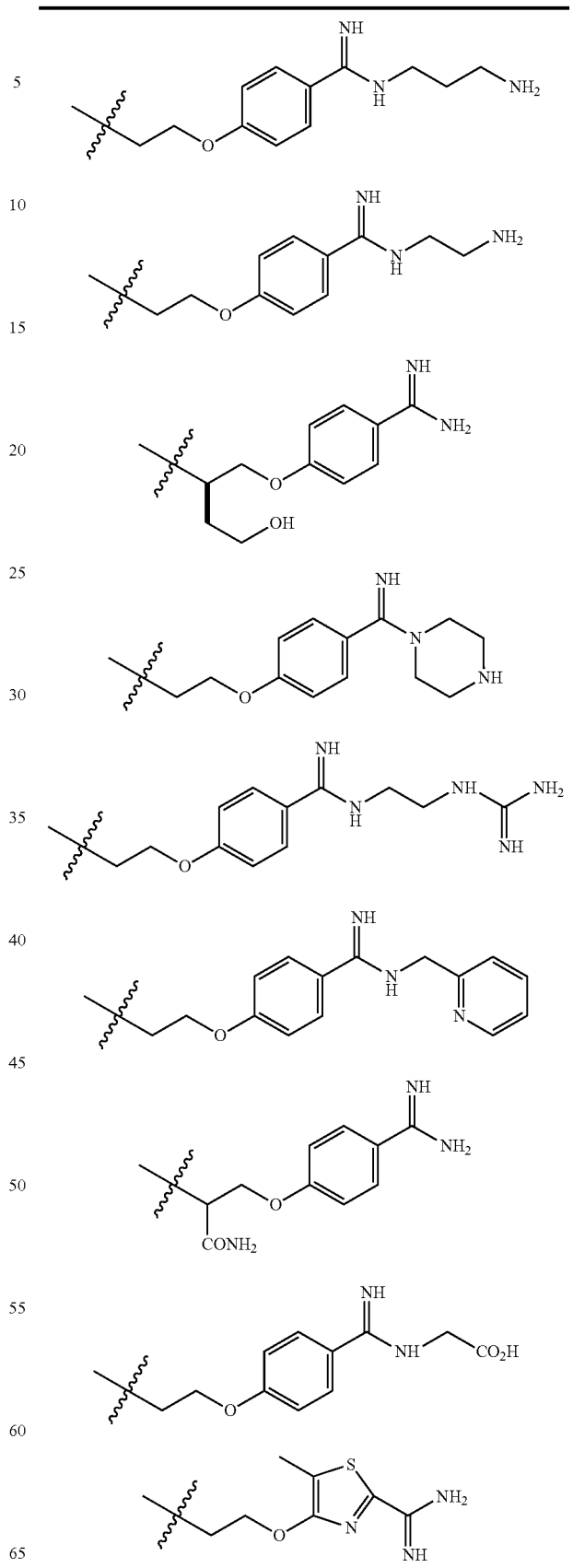

TABLE 1-continued
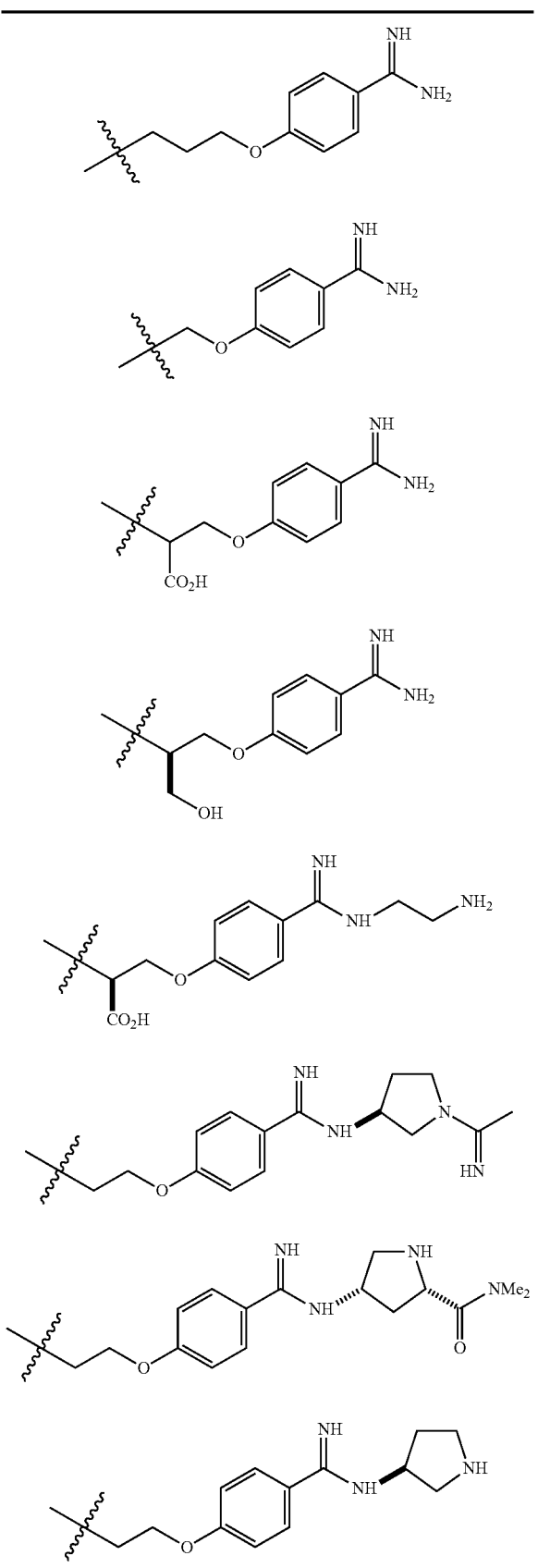
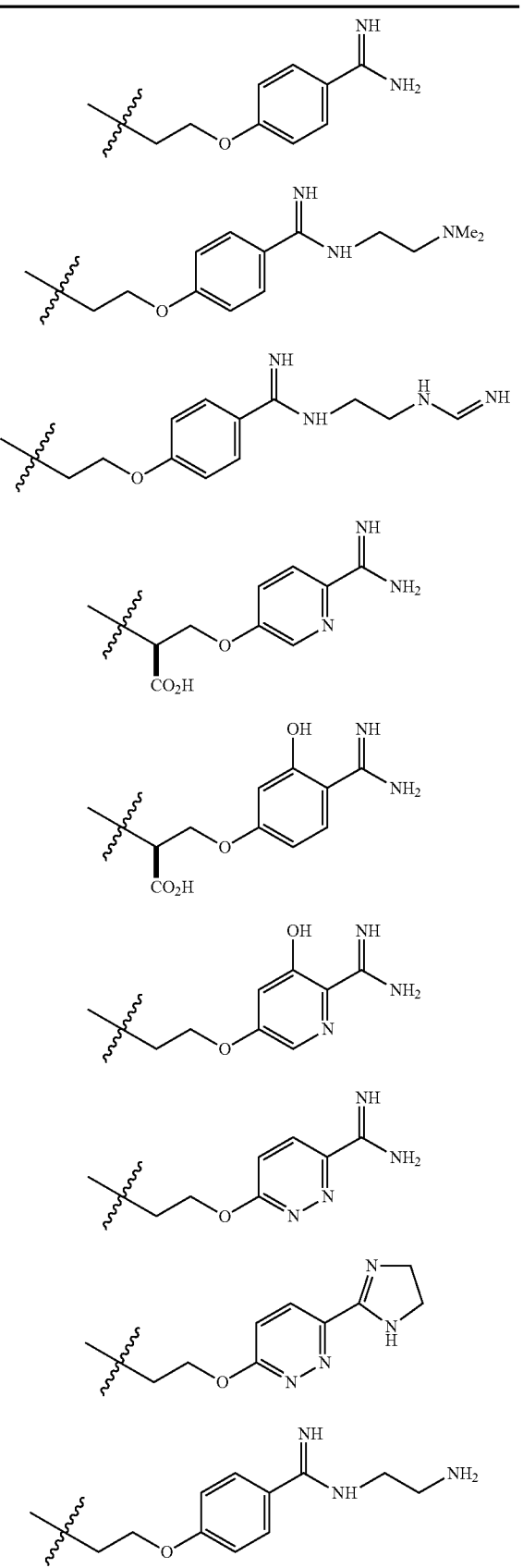

TABLE 1-continued

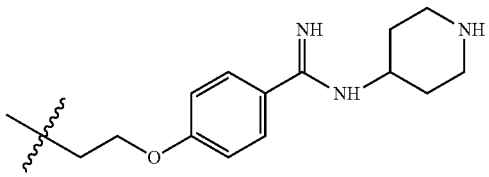 [SMILES: *CCOc1ccc(C(=N)NC2CCNCC2)cc1]

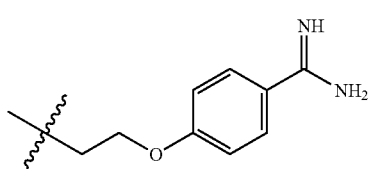 [SMILES: *CCOc1ccc(C(=N)N)cc1]

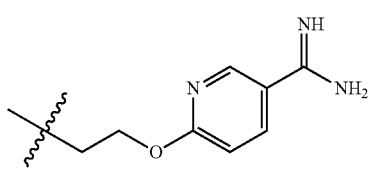 [SMILES: *CCOc1ccc(C(=N)N)cn1]

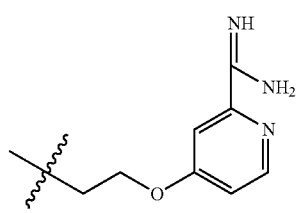 [SMILES: *CCOc1ccnc(C(=N)N)c1]

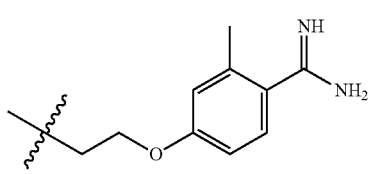 [SMILES: *CCOc1ccc(C(=N)N)c(C)c1]

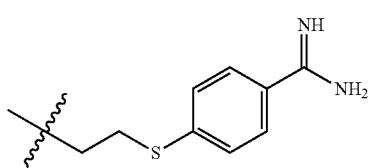 [SMILES: *CCSc1ccc(C(=N)N)cc1]

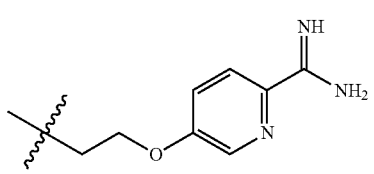 [SMILES: *CCOc1ccc(C(=N)N)nc1]

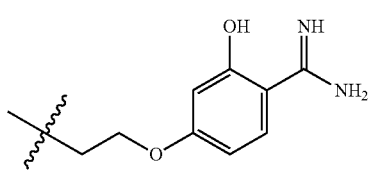 [SMILES: *CCOc1ccc(C(=N)N)c(O)c1]

TABLE 1-continued

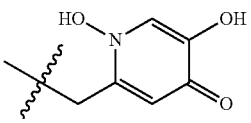 [SMILES: *Cc1cc(=O)c(O)cn1O]

—Me
—Et
—CO$_2$H
—CH$_2$C(O)NHOH
—CH$_2$C(O)NHOCPh$_3$
—CH$_2$C(O)NHOCHPh$_2$

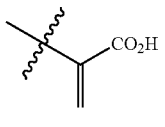 [SMILES: *C(=C)C(=O)O]

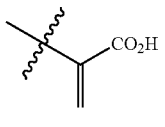 [SMILES: *C(=C)C(=O)O]

—CH$_2$CO$_2$CHPh$_2$
—CH$_2$CO$_2$CMe$_3$
or —CH(Me)$_2$.

It should be specifically noted that any or all of the non-exchangeable hydrogen atoms of the R$_6$ substituent, which are depicted above, may be substituted with deuterium and hence are within the scope of the present application.

In some of the above embodiments of Formula (I), R$_5$ is

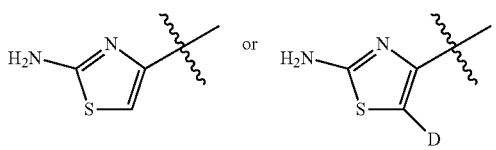

and R$_6$ is —CH$_2$CO$_2$H, —CD$_2$CO$_2$H or —CHDCO$_2$H. In other of the above embodiments, R$_5$ is

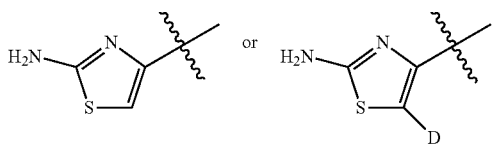 [SMILES: *c1csc(N)n1 ; *c1nc(N)sc1[2H]]

and R$_6$ is —CR$_7$R$_8$CO$_2$H, where R$_7$ and R$_8$ are independently —CH$_3$, —CD$_3$, —CD$_2$H or —CDH$_2$.

In some of the above embodiments, R$_1$ and R$_2$ are —CD$_3$. In other of the above embodiments, one of R$_1$ and R$_2$ is —CH$_3$ and the other of R$_1$ and R$_2$ is —CD$_3$. In still other of the above embodiments, R$_1$ is hydrogen and R$_2$ is —CH$_3$, —CD$_3$, —CD$_2$H or —CDH$_2$. In still other of the above embodiments, R$_1$ is deuterium and R$_2$ is —CH$_3$, —CD$_3$, —CD$_2$H or —CDH$_2$. In still other of the above embodiments, R$_2$ is hydrogen and R$_1$ is —CH$_3$, —CD$_3$, —CD$_2$H or —CDH$_2$. In still other of the above embodiments, R$_2$ is deuterium and R$_1$ is —CH$_3$, —CD$_3$, —CD$_2$H or —CDH$_2$. In still other of the above embodiments, R$_3$ is hydrogen and R$_4$ is —SO$_3$H. In still other of the above embodiments, R$_3$ is deuterium and $R_4$ is —SO$_3$H. In still other of the above embodiments, $R_3$ is hydrogen and $R_4$ is —OSO$_3$H. In still other of the above embodiments, $R_3$ is deuterium and $R_4$ is —OSO$_3$H.

Of particular interest are deuterated derivatives of tigemonam and aztreonam, the parent structures of which are depicted below. It should be noted that any or all of the non-exchangeable hydrogen atoms in tigemonam or aztreonam may be substituted with deuterium and hence are within the scope of the present invention.

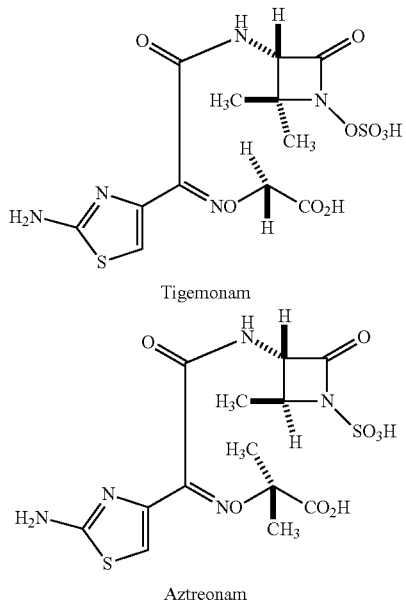

Tigemonam

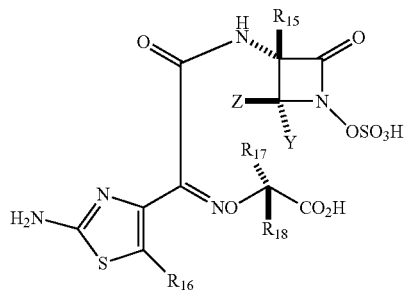

Aztreonam

In some embodiments, a compound of structural Formula (II) is provided:

(II)

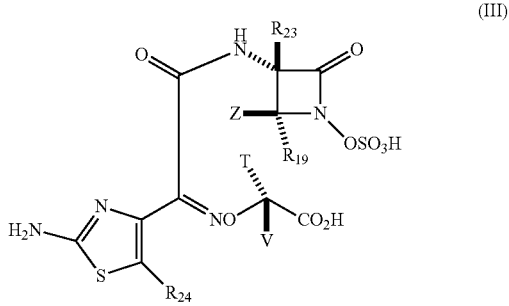

or pharmaceutically acceptable salts, hydrates, solvates and polymorphs thereof, wherein:
X is —CR$_9$R$_{10}$R$_{11}$;
Y is —CR$_{12}$R$_{13}$R$_{14}$; and
R$_9$-R$_{18}$ are independently hydrogen or deuterium, provided that at least one of R$_9$-R$_{18}$ is deuterium.

In some embodiments, R$_9$-R$_{14}$ are deuterium. In other embodiments, R$_{15}$-R$_{18}$ are deuterium. In still other embodiments, R$_9$-R$_{18}$ are deuterium. In still other embodiments, R$_9$-R$_{11}$ are deuterium. In still other embodiments, R$_{12}$-R$_{14}$ are deuterium. In still other embodiments, R$_9$-R$_{11}$ and R$_{15}$-R$_{18}$ are deuterium. In still other embodiments, R$_{12}$-R$_{14}$ and R$_{15}$-R$_{18}$ are deuterium. In still other embodiments, R$_9$-R$_{11}$ and $R_{17}$-$R_{18}$ are deuterium. In still other embodiments, $R_{12}$-$R_{14}$ and $R_{17}$-$R_{18}$ are deuterium. In still other embodiments, $R_9$-$R_{14}$ and $R_{17}$-$R_{18}$ are deuterium.

In some embodiments, R$_9$-R$_{14}$ are deuterium and R$_{15}$-R$_{18}$ are hydrogen. In other embodiments, R$_9$-R$_{14}$ are hydrogen and R$_{15}$-R$_{18}$ are deuterium. In still other embodiments, R$_9$-R$_{11}$ are deuterium and R$_{15}$-R$_{18}$ are hydrogen. In still other embodiments, R$_{12}$-R$_{14}$ are deuterium, R$_9$-R$_{11}$ are hydrogen and R$_{15}$-R$_{18}$ are hydrogen. In still other embodiments, R$_9$-R$_{11}$ and R$_{15}$-R$_{18}$ are deuterium and R$_{12}$-R$_{14}$ are hydrogen. In still other embodiments, R$_{12}$-R$_{14}$ and R$_{15}$-R$_{18}$ are deuterium and R$_9$-R$_{11}$ are hydrogen. In still other embodiments, R$_9$-R$_{11}$ and R$_{17}$-R$_{18}$ are deuterium and R$_{12}$-R$_{16}$ are hydrogen. In still other embodiments, R$_{12}$-R$_{14}$ and R$_{17}$-R$_{18}$ are deuterium and R$_9$-R$_{11}$ are hydrogen and R$_{15}$-R$_{16}$ are hydrogen. In still other embodiments, R$_9$-R$_{14}$ and R$_{17}$-R$_{18}$ are deuterium and R$_{15}$-R$_{16}$.

In some embodiments, a compound of structural Formula (III) is provided:

(III)

or pharmaceutically acceptable salts, hydrates, solvates and polymorphs thereof, wherein:
Z is —CR$_{20}$R$_{21}$R$_{22}$;
T is —CR$_{25}$R$_{26}$R$_{27}$;
T is —CR$_{28}$R$_{29}$R$_{30}$; and
R$_{19}$-R$_{30}$ are independently hydrogen or deuterium, provided that at least one of R$_{19}$-R$_{30}$ is deuterium.

In some embodiments, R$_{19}$-R$_{30}$ are deuterium. In other embodiments, R$_{25}$-R$_{30}$ and R$_{20}$-R$_{22}$ are deuterium. In still other embodiments, R$_{25}$-R$_{30}$ and R$_{19}$ are deuterium. In still other embodiments, R$_{25}$-R$_{30}$ are deuterium. In still other embodiments, R$_{29}$-R$_{22}$ deuterium. In still other embodiments, R$_{25}$-R$_{30}$, R$_{20}$-R$_{22}$ and R$_{19}$ are deuterium. In still other embodiments, R$_{20}$-R$_{22}$ are deuterium. In still other embodiments, R$_{19}$ is deuterium. In still other embodiments, R$_{23}$-R$_{24}$ are deuterium.

In some embodiments, R$_{25}$-R$_{30}$ and R$_{20}$-R$_{22}$ are deuterium and R$_{19}$-R$_{21}$ and R$_{23}$-R$_{24}$ are hydrogen. In still other embodiments, R$_{25}$-R$_{30}$ and R$_{19}$ are deuterium and R$_{20}$-R$_{24}$ are hydrogen. In still other embodiments, R$_{25}$-R$_{30}$ are deuterium and R$_{19}$-R$_{24}$ are hydrogen. In still other embodiments, R$_{19}$-R$_{22}$ are deuterium and R$_{24}$-R$_{30}$ are hydrogen. In still other embodiments, R$_{25}$-R$_{30}$, R$_{20}$-R$_{22}$ and R$_{19}$ are deuterium and R$_{23}$-R$_{24}$ are hydrogen. In still other embodiments, R$_{20}$-R$_{22}$ are deuterium and R$_{23}$-R$_{30}$ and R$_{19}$ are hydrogen are hydrogen. In still other embodiments, R$_{19}$ is deuterium and R$_{20}$-R$_{30}$ are hydrogen. In still other embodiments, R$_{23}$-R$_{24}$ are deuterium and R$_{19}$-R$_{22}$ are hydrogen and R$_{25}$-R$_{30}$ are hydrogen.

Some exemplary compounds of Formulae (I), (II) and (III), which are deuterated aztreonam and tigemonam derivatives are shown in Table 2, below.

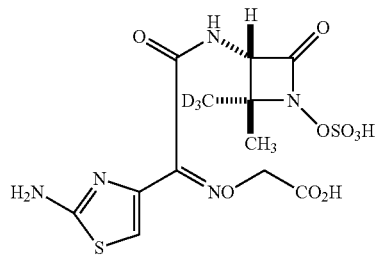
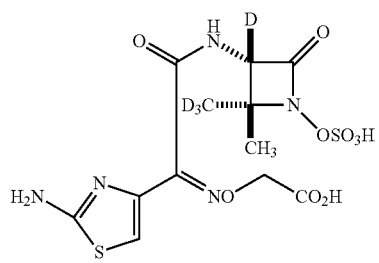
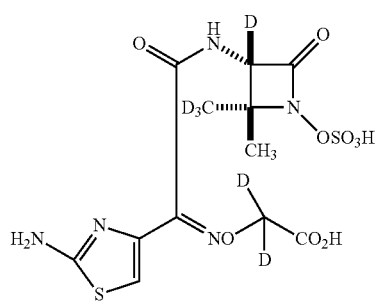
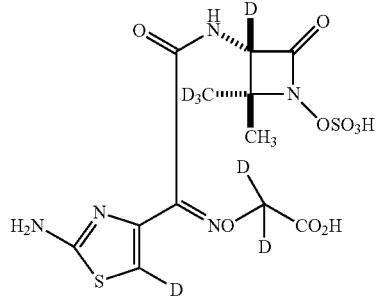
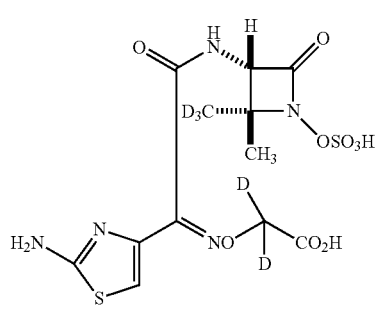
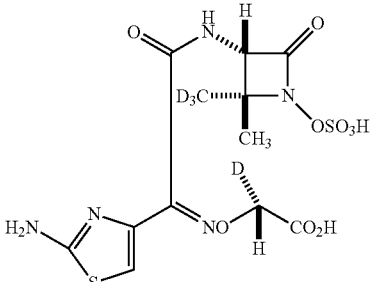
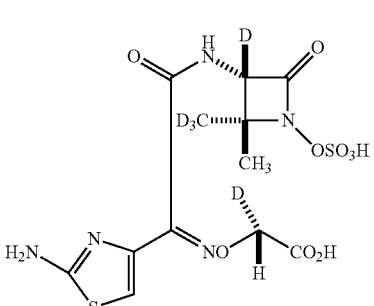
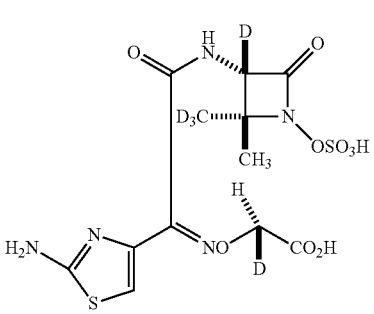
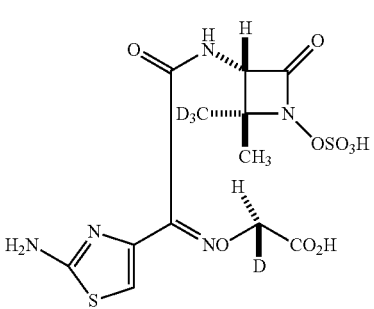
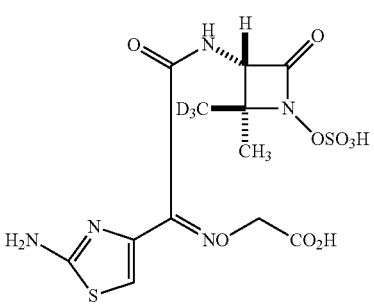

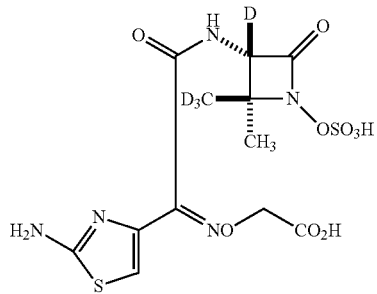
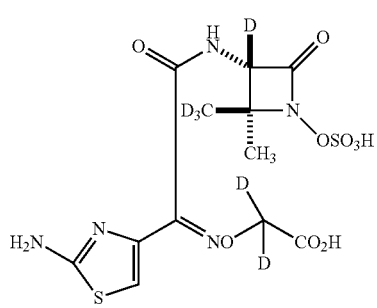
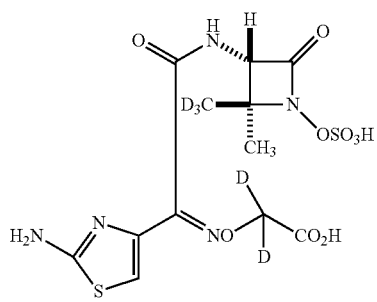
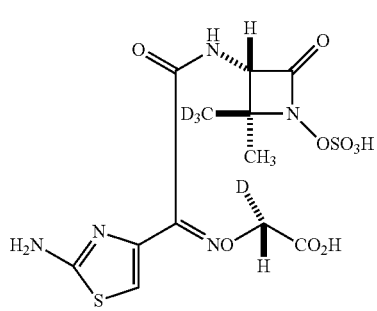
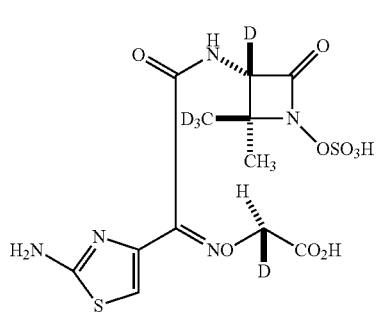
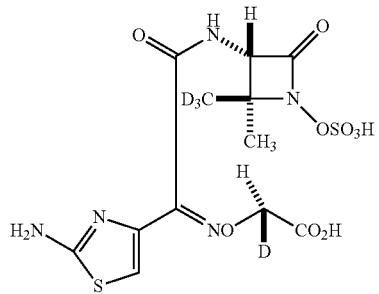
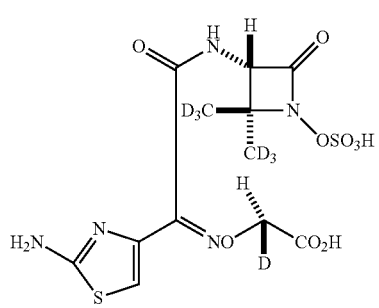
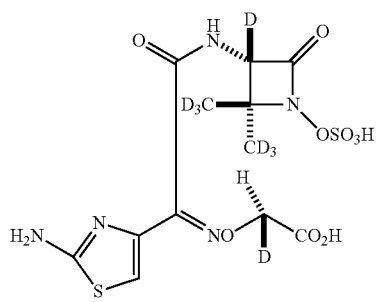
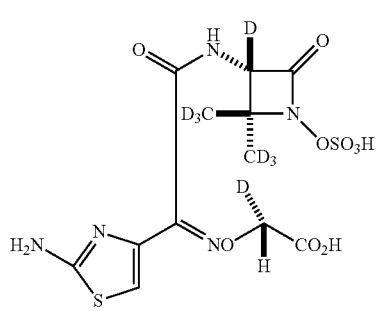
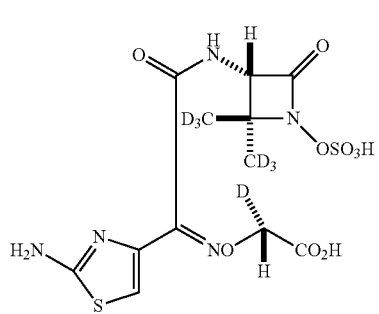

| 29 -continued | 30 -continued |
|---|---|
| 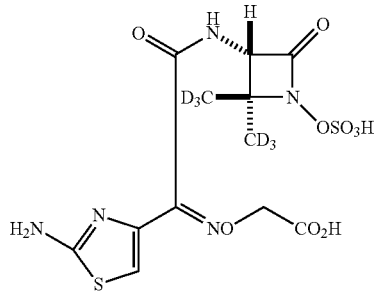 | 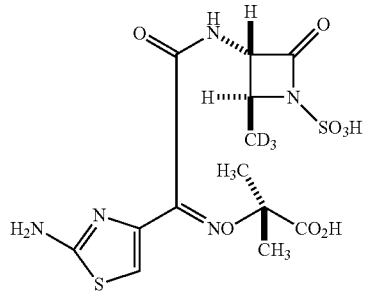 |
| 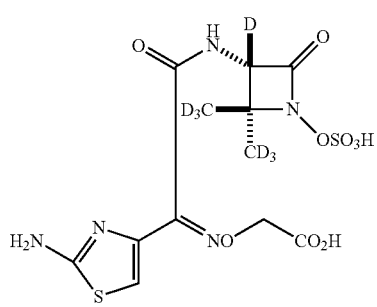 | 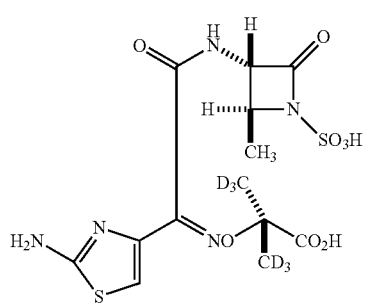 |
| 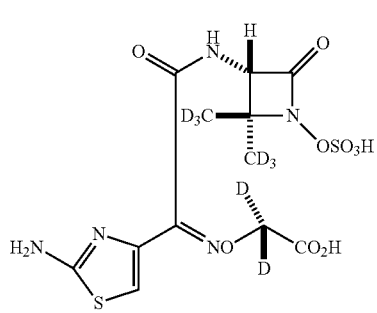 | 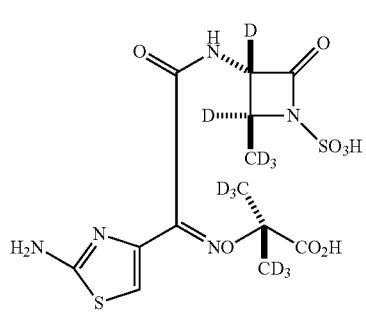 |
| 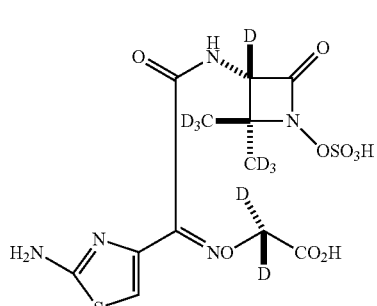 | 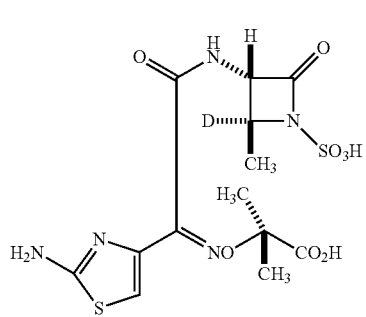 |
| 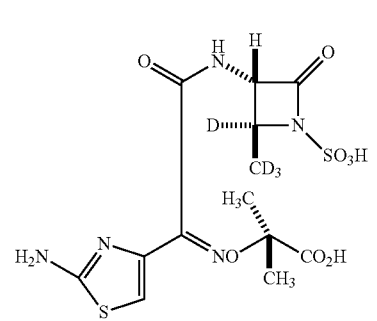 |  |

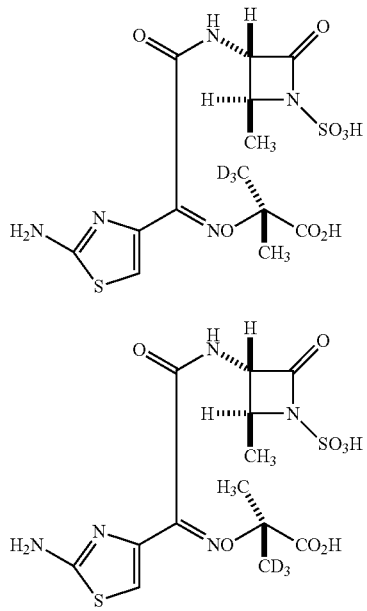

Other deuterated aztreonam and tigemonam structures, which are not depicted above will be immediately obvious to the skilled artisan and are also within the scope of the present application.

Isotopic hydrogen can be introduced into compounds disclosed herein by synthetic techniques that employ deuterated reagents, whereby incorporation rates are predetermined; and/or by exchange techniques, wherein incorporation rates are determined by equilibrium conditions, and may be highly variable depending on the reaction conditions. Synthetic techniques, where deuterium is directly and specifically inserted by deuterated reagents of known isotopic content, may yield high deuterium abundance, but can be limited by the chemistry required. Exchange techniques, on the other hand, may yield lower deuterium incorporation, often with the isotope being distributed over many sites on the molecule.

Figure 3:
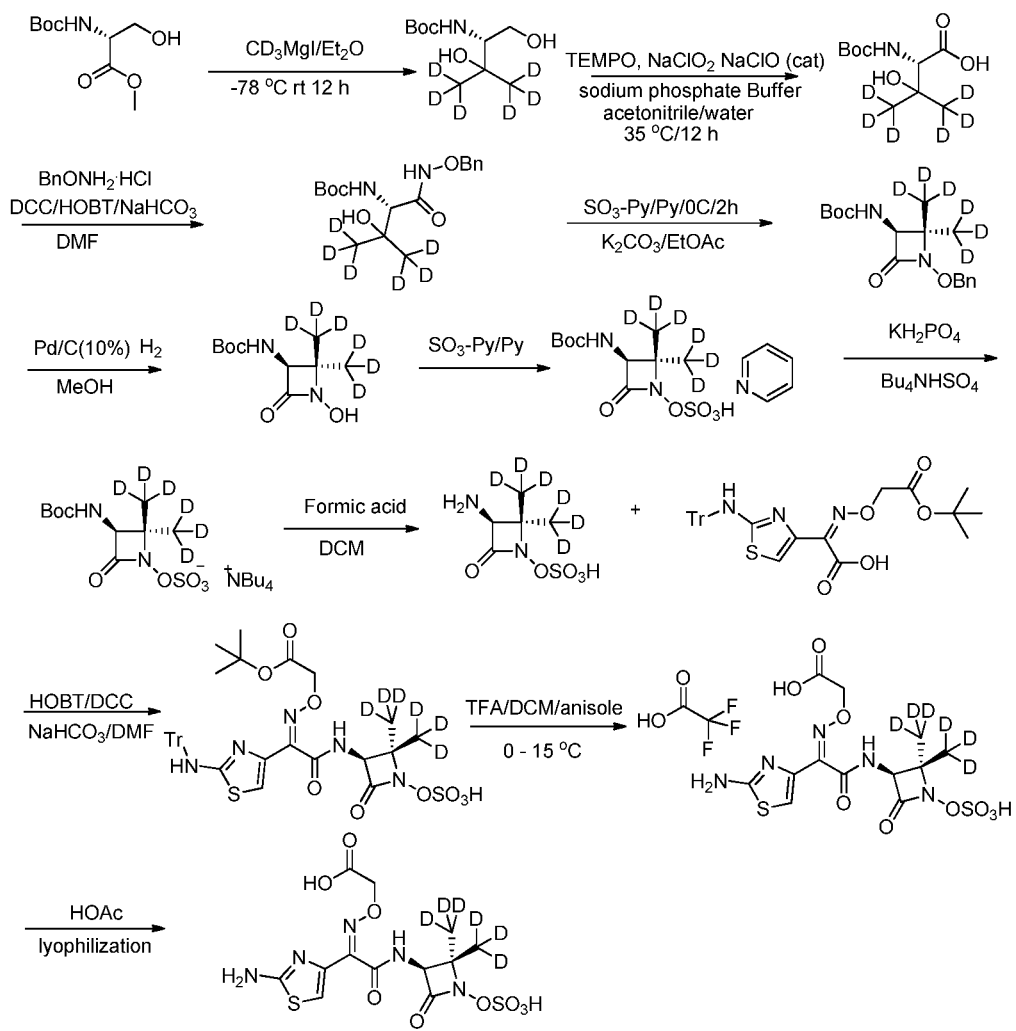
FIG. 3 is a scheme which describes the synthesis of (S,Z)-2-(((1-(2-aminothiazol-4-yl)-2-((2,2-dimethyl-$d_6$-4-oxo-1-(sulfooxy)azetidin-3-yl)amino)-2-oxoethylidene)amino)oxy)acetic acid.
Figure 4:
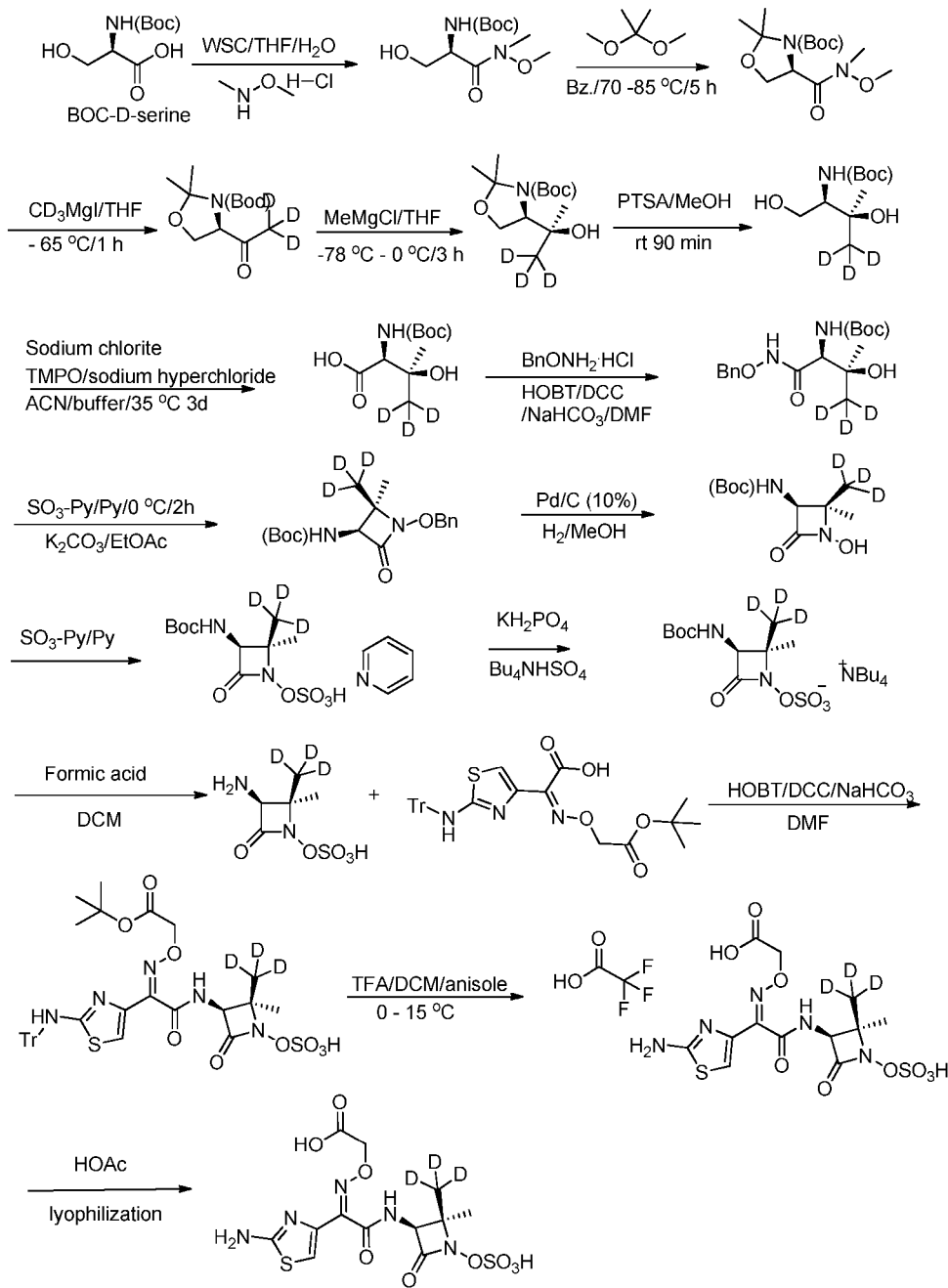
FIG. 4 is a scheme which describes the synthesis of 2-(((Z)-(1-(2-aminothiazol-4-yl)-2-(((2R,3S)-2-$d_3$-2-methyl-4-oxo-1-(sulfooxy)azetidin-3-yl)amino)-2-oxoethylidene)amino)oxy)acetic acid.
Figure 5:
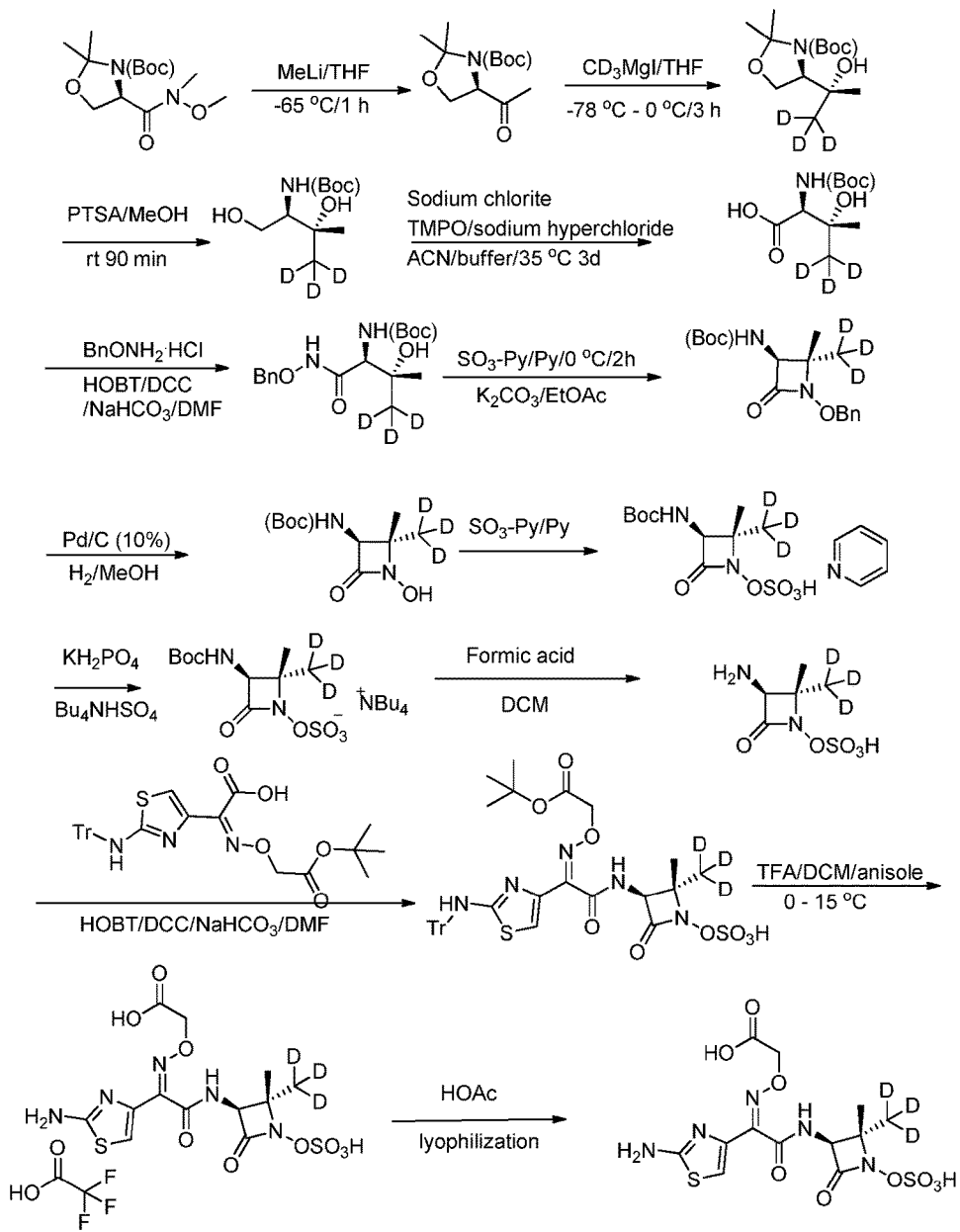
FIG. 5 is a scheme which describes the synthesis of 2-(((Z)-(1-(2-aminothiazol-4-yl)-2-(((2S,3S)-2-($d_3$-methyl-2-methyl-4-oxo-1-(sulfooxy)azetidin-3-yl)amino)-2-oxoethylidene)amino)oxy)acetic acid.

The compounds, as disclosed herein, can be prepared by methods known to one of skill in the art and routine modifications thereof, and/or following procedures similar to those described in the Example section herein or schemes described in FIGS. 3-5 and routine modifications thereof, and/or procedures found in WO 2014014841; WO 2013185112; WO 2012170061; WO 2011133956; WO 2011133751; WO 2011119984; WO 2010054138; WO 2010053471; US 201301162389 US 20120046330; US 201200159999 US 20090131492, which are hereby incorporated in their entirety, and references cited therein and routine modifications thereof. Exemplary methods for the synthesis of some deuterated tigemonam derivatives are illustrated in FIGS. 3-5 and these, for example, could be adapted by the skilled artisan to produce more complex deuterated derivatives, by example using various deuterated side chains when coupling to the lactam core.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073, 543; 5,639,476; 5,354,556; 5,639,480; 5,733,566; 5,739, 108; 5,891,474; 5,922,356; 5,972,891; 5,980,945; 5,993, 855; 6,045,830; 6,087,324; 6,113,943; 6,197,350; 6,248, 363; 6,264,970; 6,267,981; 6,376,461; 6,419,961; 6,589, 548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984)). In some embodiments, a controlled release device is introduced into a subject in proximity of the site of inappropriate immune activation or a tumor. Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest, herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder.

Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agents. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carriers. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), the MIC as determined in cell culture (i.e., the minimal inhibitory concentration for growth) or the $IC_{100}$ as determined in cell culture (i.e., the concentration of antimicrobial sulfonamide derivative that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known antimicrobial agents by comparing the $IC_{50}$, MIC and/or $I_{100}$ of the specific compound disclosed herein with that of a known antimicrobial agent, and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, In: *The Pharmacological Basis of Therapeutics*, Ch. 1, p. 1).

The therapy may be repeated intermittently while infections are detectable, or even when they are not detectable. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

The compounds and compositions described herein can be used in a wide variety of applications to treat or prevent infectious diseases in a subject. The methods generally involve administering therapeutically effective amounts of deuterated O-sulfated beta-lactam hydroxamic acids and/or deuterated N-sulfated beta-lactams, or a pharmaceutical composition thereof to the subject.

In some embodiments, the infectious disease is a bacterial infection. In other embodiments, the bacterial infection is an infection with a Gram-negative bacterium. In still other embodiments, the Gram-negative bacteria is of one of the following genera: *Acinetobacter, Aeromonas, Bacteroides, Burkholderia, Citrobacter, Enterobacter, Escherichia, Fusobacterium, Haemophilus, Klebsiella, Moraxella, Morganella, Mycoplasma, Neisseria, Pantoea, Pasteurella, Plesiomonas, Porphyromonas, Prevotella, Proteus, Providencia, Pseudomonas, Salmonella, Serratia, Shigella, Spirillum, Stenotrophomonas, Streptobacillus, Treponema*, or *Yersinia*. In still other embodiments, the Gram negative bacteria of is one of the following species: *Acinetobacter baumannii, Aeromonas hydrophila, Arizona hinshawii, Bacteroides fragilis, Branhamella catarrhalis, Burkholderia cepacia, Citrobacter diversus, Citrobacter freundii, Enterobacter aerogenes, Enterobacter cloacae, Escherichia coli, Fusobacterium nucleatum, Haemophilus influenzae, Haemophilus parainfluenzae, Klebsiella oxytoca, Klebsiella pneumoniae, Moraxella catarrhalis, Morganella morganii, Neisseria gonorrhoeae, Neisseria meningitidis, Pantoea agglomerans, Pasteurella multocida, Plesiomonas shigelloides, Prevotella melaninogenica, Proteus mirabilis, Proteus rettgeri, Proteus vulgaris, Pseudomonas aeruginosa, Pseudomonas diminuta, Pseudomonas fluorescens, Pseudomonas stutzeri, Salmonella enterica, Salmonella enteritidis, Salmonella typhi, Serratia marcescens, Spirillum minus, Stenotrophomonas maltophilia, Streptobacillus moniliformis, Treponema pallidum*, or *Yersinia enterocolitica*.

The compounds and compositions described herein may be used treat or prevent various diseases caused by the above bacteria. These include, but are not limited to, venereal disease, pneumonia, complicated urinary tract infections, urinary tract infections, complicated intra-abdominal infections and intra-abdominal infections. The compounds and compositions described herein may also be used kill bacteria described above. In some embodiments, the compounds and/or compositions are effective against gram positive and anaerobic bacteria.

Additionally, the development of antibiotic resistance continues to grow as a problem facing patients and clinicians. Accordingly, the US Food and Drug Administration has identified the following pathogens as presenting a potentially serious threat to public health: *Acinetobacter* species, *Aspergillus* species, *Burkholderia cepacia* complex, *Campylobacter* species, *Candida* species, *Clostridium difficile*, *Coccidioides* species, *Cryptococcus* species, *Enterobacteriaceae* (e.g., *Klebsiella pneumoniae*), *Enterococcus* species, *Helicobacter pylori*, *Mycobacterium tuberculosis* complex, *Neisseria gonorrhoeae*, *N. meningitidis*, non-tuberculous mycobacteria species, *Pseudomonas* species, *Staphylococcus aureus*, *Streptococcus agalactiae*, *S. pneumoniae*, *S. pyogenes*, and *Vibrio cholerae*. The FDA has designated these organisms "qualifying pathogens" for purposes of the Generating Antibiotic Incentives Now (GAIN) Act, intended to encourage development of new antibacterial and antifungal drugs for the treatment of serious or life threatening infections. The methods, kits, etc. disclosed herein are useful for the treatment of diseases, infections, etc. caused by many of these organisms as well.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of infectious disease. In some embodiments, the compounds and pharmaceutical compositions disclosed herein are administered with β-lactamase inhibitors and/or carbapenemase inhibitors or pharmaceutical compositions thereof. Exemplary β-lactamase inhibitors and/or carbapenemase inhibitors are well known to those of skill in the art and include, for example, clavulanic acid, sulbactam, avibactam, tazobactam, relebactam, vaborbactam, ETX 2514, RG6068 (i.e., OP0565) (Livermore et al., *J AntiMicrob Chemother* 2015, 70: 3032) and RPX7009 (Hecker et al., *J Med Chem* 2015 58: 3682-3692). In other embodiments, the compounds and pharmaceutical compositions disclosed herein are administered with lindamycin, erythromycin, metronidazole, penicillins, or vancomycin or pharmaceutical compositions thereof. In still other embodiments, the compounds and pharmaceutical compositions disclosed herein are administered with administered with β-lactamase inhibitors and/or carbapenemase inhibitors or pharmaceutical compositions thereof and lindamycin, erythromycin, metronidazole, penicillins, or vancomycin or pharmaceutical compositions thereof.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided herein are administered prior to or subsequent to the one or more additional active ingredients.

The following examples are provided for illustrative purposes only and are not intended to limit the scope of the invention.

EXAMPLES

Example 1: $d_6$-(R)-tert-butyl (1,3-dihydroxy-3-methylbutan-2-yl)carbamate

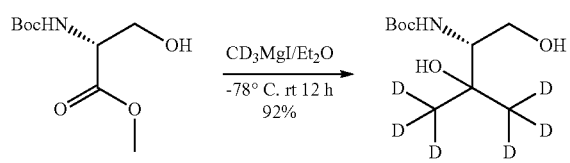 [SMILES: COC(=O)[C@@H](CO)NC(=O)OC(C)(C)C ; [2H]C([2H])([2H])C(O)([C@@H](CO)NC(=O)OC(C)(C)C)C([2H])([2H])[2H]]

A 1 M solution of $d_3$-Methylmagnesium iodide (200 ml, 200.0 mmol, 5.9 equiv.) in diethyl ether was added dropwise to a cooled solution of N-(tert-butoxycarbonyl)-D-serine (7.44 g, 33.9 mmol, 1.0 equiv.) in diethyl ether (12 ml) at −78° C. within 10 min. The reaction mixture was allowed to reach r.t. and stirred at r.t. for 12 h at which point TLC and crude $^1$H NMR indicated the reaction was complete. The reaction mixture was poured into a saturated aqueous ammonium chloride solution (250 mL). The organic layer was separated and the aqueous layer was extracted with ethyl acetate (3×150 mL). The combined organic layers were dried over anhydrous sodium sulfate, filtered and concentrated. The resulting material was used directly without purification (7 g, 92%). $^1$HNMR (300 MHz, CDCl$_3$), δ 5.36 (m, 1H), 4.05-4.01 (m, 1H), 3.84-3.78 (m, 1H), 3.48-3.45 (m, 1H), 2.53-2.44 (m, 2H), 1.45 (s, 9H).

Example 2: Synthesis of $d_6$-(S)-2-((tert-butoxycarbonyl)amino)-3-hydroxy-3-methylbutanoic acid

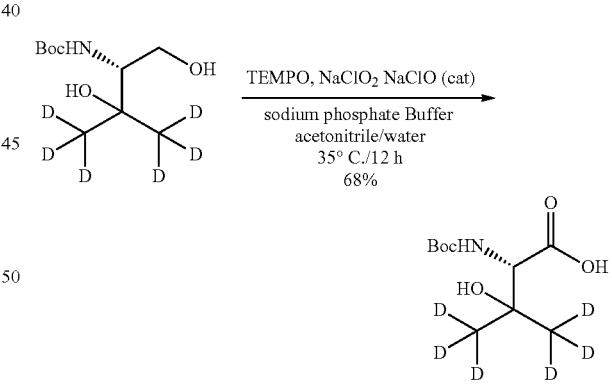

TEMPO (0.49 g, 3.1 mmol, 0.1 equiv.) was added to a mixture of $d_6$-(R)-tert-butyl (1,3-dihydroxy-3-methylbutan-2-yl)carbamate (7 g, 31.1 mmol, 1.0 equiv.) in acetonitrile (155 mL) and sodium phosphate buffer (126 mL, 0.7 M). The resulting mixture was heated to 35° C. and then treated by simultaneous addition of 80.0% sodium chlorite (9.1 g, 80.8 mmol, 2.6 equiv.) solution in water (25 mL) and 4 drops of a very dilute sodium hypochlorite (has to be freshly made or at least within 3 days, 3 mL of commercial solution in 100 mL of water), stirred at 35° C. overnight, cooled to r.t., treated with citric acid (6.4 g, 33.3 mmol, 1.1 equiv.) (pH 3), saturated with sodium chloride and extracted with ethyl acetate (280 ml) (3×). The organic extracts were combined and sodium carbonate solution was added (2M (314 ml, 627.7 mmol, 20.2 equiv.)) and stirred overnight. After separation, the aqueous layer was extracted with ethyl acetate again. The aqueous layer was cooled to 0° C., the pH was adjusted to 3.0 using 4 M solution of $H_3PO_4$ (313 mL) and the solution was saturated with sodium chloride. The resulting mixture was extracted with ethyl acetate (280 ml) (3×), the organic phases were combined, dried, filtered and concentrated under reduced pressure to give the title compound as a white solid (5.02 g, 68%). $^1$HNMR (300 MHz, DMSO-d6), δ 6.52 (d, J=8.7 Hz, 1H), 3.84 (d, J=9.0 Hz, 1H), 1.38 (s, 9H).

Example 3: Synthesis of $d_6$-(S)-tert-butyl (1-((benzyloxy)amino)-3-hydroxy-3-methyl-1-oxobutan-2-yl)carbamate

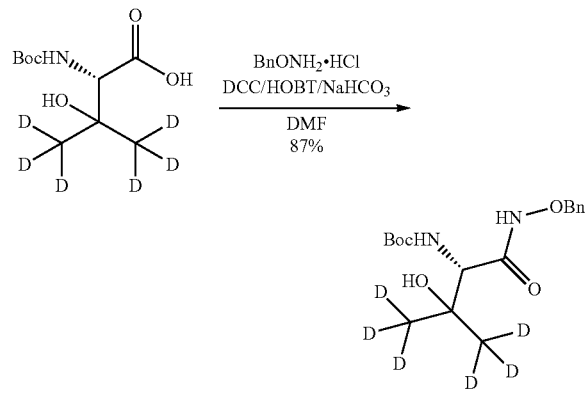

N,N'-dicyclohexylcarbodiimide (5.9 g, 28.4 mmol, 1.1 equiv.) was added to a solution of $d_6$-(S)-2-((tert-butoxycarbonyl)amino)-3-hydroxy-3-methylbutanoic acid (6.0 g, 25.2 mmol, 1.0 equiv.) in N,N-dimethylformamide (80 ml) at r.t. followed by 1-hydroxybenzotriazole (3.8 g, 28.4 mmol, 1.1 equiv.). The resulting mixture was stirred at r.t. for 30 min, and 98.0% O-benzylhydroxylamine hydrochloride (4.7 g, 28.6 mmol, 1.1 equiv.) was added followed by sodium bicarbonate (5.4 g, 64.5 mmol, 2.6 equiv.). The reaction mixture was stirred at rt for 24 h and filtered through a Celite pad, washed with ethyl acetate (2×50 mL), and concentrated under reduced pressure at 40-50° C. The residue was diluted with dichloromethane (170 mL), loaded to a silica gel column (40 g, 30-40% ethyl acetate/hexanes) to give the title compound as a semi-solid after elution. The semi-solid was sonicated with ethyl acetate and concentrated on an oil pump for 2 h to give a white solid (7.5 g, 87%). $^1$HNMR (300 MHz, $CDCl_3$), δ 9.11 (s, 1H), 7.38-7.36 (m, 5H), 5.55 (d, J=8.7 Hz, 1H), 4.90 (s, 2H), 3.66 (d, J=8.7 Hz, 1H), 1.43 (s, 9H).

Example 4: Synthesis of (S)-tert-butyl(1-(benzyloxy)-2,2-dimethyl-$d_6$-4-oxoazetidin-3-yl)carbamate

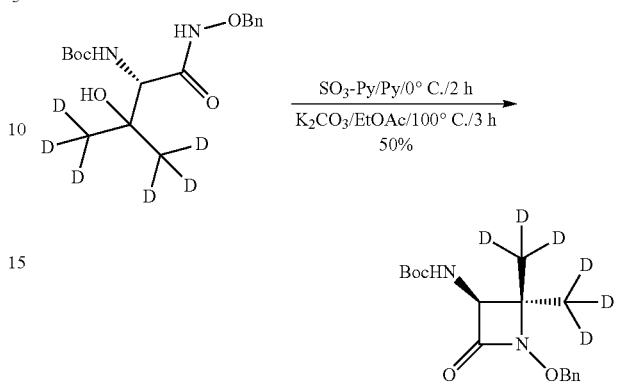

Sulfur trioxide pyridine complex (1.8 g, 11.3 mmol, 1.4 equiv.) was added to a solution of $d_6$-(S)-tert-butyl (1-((benzyloxy)amino)-3-hydroxy-3-methyl-1-oxobutan-2-yl) carbamate (2.7 g, 7.9 mmol, 1.0 equiv.) in pyridine (27 ml) at 0° C. in portions and the mixture was stirred for 2 h. The pyridine was removed in vacuo and the residue was triturated with diethyl ether/hexanes (1:10, 50 mL) to remove the major portion of pyridine. A solution of potassium carbonate (6.8 g, 49.0 mmol, 6.2 equiv.) in water (33 ml) and ethyl acetate (24 ml) were added to the solid intermediate. The resulting mixture was heated under reflux (100° C.) for 3 h. The organic layer was separated, the aqueous layer was extracted with ethyl acetate (2×, total 600 mL), the combined organic layers were washed with brine, dried over anhydrous sodium sulfate, filtered and concentrated. The material was dissolved in dichloromethane and load to a silica gel column (25 g, 30-40% ethyl acetate/hexanes) to afford the title compound as a white powder after elution (1.28 g, 50%). $^1$HNMR (300 MHz, DMSO-d6), δ 7.73 (d, J=8.7 Hz, 1H), 7.41-7.38 (m, 5H), 4.92 (s, 2H), 4.25 (d, J=8.7 Hz, 1H), 1.38 (s, 9H).

Example 5: Synthesis of (S)-tert-Butyl (1-hydroxy-2,2-dimethyl-$d_6$-4-oxoazetidin-3-yl)carbamate

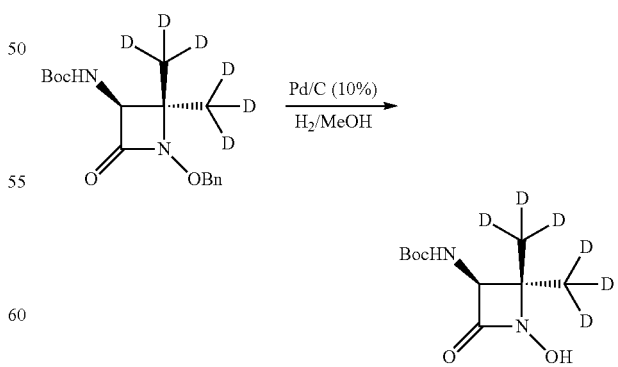

10.0% palladium on carbon (0.4 g, 0.4 mmol, 0.1 equiv.) (wet, ~50% water) was added to a solution of (S)-tert-butyl (1-(benzyloxy)-2,2-dimethyl-$d_6$-4-oxoazetidin-3-yl)carbamate (1.28 g, 3.9 mmol, 1.0 equiv.) in methanol (25 mL)

and the mixture was hydrogenated under hydrogen balloon at r.t. for 12 h. The reaction was then degassed, blanketed with argon and filtered through a Celite pad which was rinsed with methanol (2×). The filtrate was concentrated in vacuo to give an oil which was triturated with 10% ether in hexanes, filtered and dried in vacuum to give the title compound as a white solid (quant.). $^1$HNMR (300 MHz, DMSO-d6), δ 9.99 (brs, 1H), 7.70 (d, J=8.1 Hz, 1H), 4.19 (d, J=9.0 Hz, 1H), 1.39 (s, 9H).

Example 6: Synthesis of (S)-3-amino-2,2-dimethyl-d$_6$-4-oxoazetidin-1-yl hydrogen sulfate

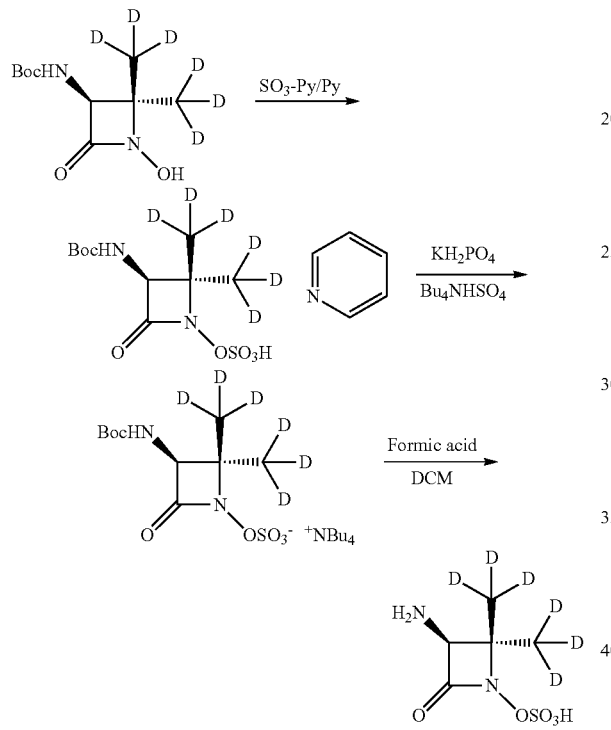

Sulfur trioxide pyridine complex (0.75 g, 4.7 mmol, 1.2 equiv.) was added to a solution of (S)-tert-butyl (1-hydroxy-2,2-dimethyl-d$_6$-4-oxoazetidin-3-yl)carbamate (0.93 g, 3.9 mmol, 1.0 equiv.) in pyridine (9 mL) at 0° C. The resulting mixture was stirred at r.t. for 1.5 h and concentrated in vacuo to give the pyridinium salt as a foam that is used directly next step.

Pyridine (S)-3-((tert-butoxycarbonyl)amino)-2,2-dimethyl-d$_6$-4-oxoazetidin-1-yl sulfate (1.55 g, 3.9 mmol, 1.0 equiv.) was dissolved in 0.5 M potassium phosphate monobasic (5.4 g, 39.8 mmol, 10.2 equiv.) in water (77 mL) solution. The mixture was extracted with dichloromethane (2×20 mL). The aq. layer was cooled to 0° C. and 98.0% tetrabutylammonium hydrogen sulfate (1.59 g, 4.6 mmol, 1.2 equiv.) was added to give a white suspension. The resulting mixture was stirred at r.t. for 1 h and extracted with dichloromethane (5×60 mL). The combined dichloromethane layers were dried over anhydrous magnesium sulfate, filtered and concentrated in vacuo to give the tetrabutylammonium salt which was used directly without purification.

Tetrabutylammonium (S)-3-((tert-butoxycarbonyl)amino)-2,2-dimethyl-d$_6$-4-oxoazetidin-1-yl sulfate (2.19 g, 3.9 mmol, 1.0 equiv.) was transferred to a pear shaped flask (250 mL), the residue dissolved in formic acid (6 ml) and the resulting solution was stirred at rt for 3 h. A white precipitate formed and the mixture was stirred at rt for an additional 2 h, dichloromethane was added and the mixture was placed in a −20° C. refrigerator for 3 days. The resulting solid was filtered and rinsed with cold dichloromethane to afford the title compound as a white solid (0.195 g, 23% over three steps). $^1$HNMR (300 MHz, DMSO-d6), δ 8.76 (brs, 2H), 4.16 (s, 1H).

Example 7: Synthesis of (S,Z)-tert-butyl 2-(((2-((2,2-dimethyl-d$_6$-4-oxo-1-(sulfooxy)azetidin-3-yl)amino)-2-oxo-1-(2-(tritylamino)thiazol-4-yl)ethylidene)amino)oxy)acetate

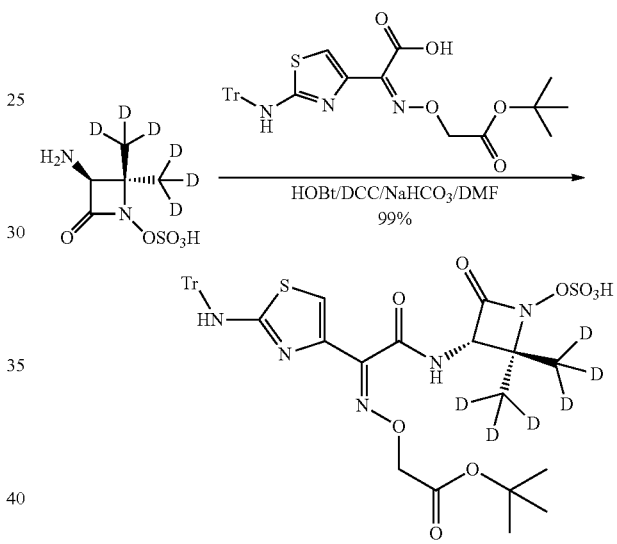

N,N'-dicyclohexylcarbodiimide (0.21 g, 1.0 mmol, 1.1 equiv.) was added to a solution of (Z)-2-((2-(tert-butoxy)-2-oxoethoxy)imino)-2-(2-(tritylamino)thiazol-4-yl)acetic acid (0.531 g, 1.0 mmol, 1.1 equiv.) in N,N-dimethylformamide (7 ml) at r.t. followed by 1-hydroxybenzotriazole (0.14 g, 1.0 mmol, 1.1 equiv.). The resulting mixture was stirred at rt for 30 min, and (S)-3-amino-2,2-dimethyl-d$_6$-4-oxoazetidin-1-yl hydrogen sulfate (0.192 g, 0.9 mmol, 1.0 equiv.) was added followed by sodium bicarbonate (0.298 g, 3.6 mmol, 4.0 equiv.). The resulting mixture was stirred at r.t. overnight and concentrated in vacuo at 40° C. (triturated with methanol, dichloromethane) to dryness. The residue was dissolved in dichloromethane and loaded to a silica gel column (25 g, 5-10% MeOH/dichloromethane) to afford the title compound (0.65 g, 99%). $^1$HNMR (300 Hz, CD$_3$OD), δ 7.36-7.26 (m, 15H), 6.82 (s, 1H), 4.74 (s, 1H, 4.61 (s, 2H), 1.49 (s, 9H).

Example 8: Synthesis of TFA salt of (S,Z)-2-(((1-(2-aminothiazol-4-yl)-2-((2,2-dimethyl-d₆-4-oxo-1-(sulfooxy)azetidin-3-yl)amino)-2-oxoethylidene)amino)oxy)acetic acid

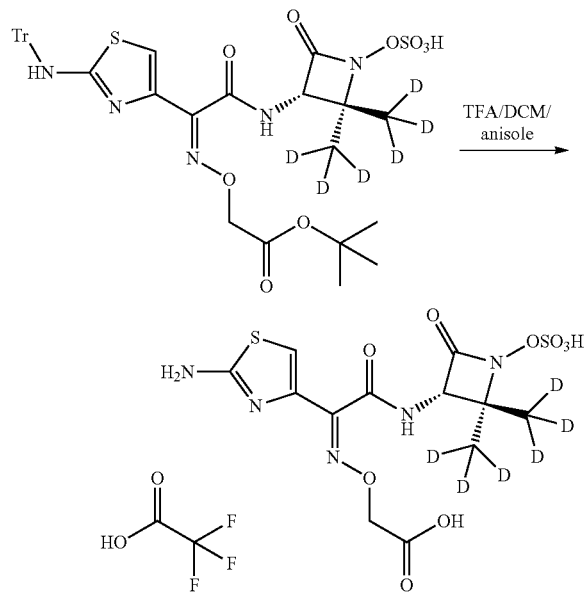

(S,Z)-tert-butyl 2-(((2-(((2,2-dimethyl-d₆-4-oxo-1-(sulfooxy)azetidin-3-yl)amino)-2-oxo-1-(2-(tritylamino)thiazol-4-yl)ethylidene)amino)oxy)acetate (0.147 g, 0.2 mmol, 1.0 equiv.) and anisole (5 ul, 0.04 mmol, 0.2 equiv.) and dry dichloromethane (0.7 ml) were charged into a flask with a stir bar under argon. The suspension was cooled to 0° C. and trifluoroacetic acid (0.7 ml, 9.4 mmol, 47.6 equiv.) was added dropwise within 5 min. The suspension became a yellow solution once TFA was added. The ice-bath was allowed to warm to up to 15° C. within 4 h. The reaction mixture was cooled to 0° C. with an ice-bath and cold deionized water (2 mL) was added dropwise. After separation, the aqueous layer was lyophilized in a 25 mL round bottom flask for 3 days. The resulting light yellow solid was added to acetonitrile and DCM and sonicated to give a white suspension. The solid was filtered and then transferred back to the original flask and freeze-dried overnight to give a fluffy white solid (84 mg, 76%).

Example 9: Removal of TFA

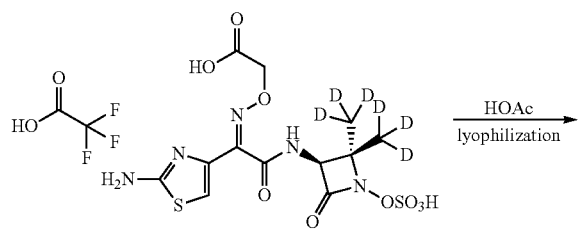

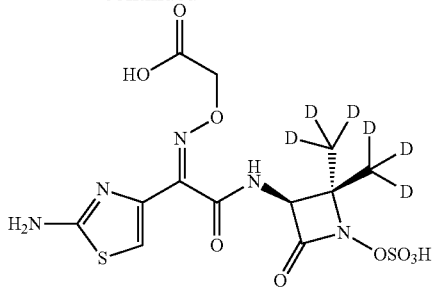

(S,Z)-2-(((1-(2-aminothiazol-4-yl)-2-(((2,2-dimethyl-d₆-4-oxo-1-(sulfooxy)azetidin-3-yl)amino)-2-oxoethylidene)amino)oxy)acetic acid (unspecified amount) was dissolved in D₂O (650 uL) and analyzed by ¹H and ¹⁹F NMR with TFE (3 uL) and then transferred to a 20 mL vial and cooled to 0° C. and glacial acetic acid (1 mL) was added. The resulting solution was stirred at 0° C. for 30 min. The resulting mixture was lyophilized for 2 days. The process was repeated eight times to afford the title compound (21.8 mg, 87.2%). TFA 4.6% by weight determined by ¹H and ¹⁹F NMR. There were no visible acetic acid protons by ¹H NMR. ¹HNMR (300 MHz, D₂O), δ 7.07 (s, 1H), 4.89 (s, 1H), 4.73 (s, 2H, overlapped with water), ¹⁹FNMR (282 MHz, D₂O), δ −75.56. LCMS: [M+1]⁺, 444.4.

Example 10: Synthesis of (R)-tert-butyl(3-hydroxy-1-(methoxy(methyl)amino)-1-oxopropan-2-yl)carbamate

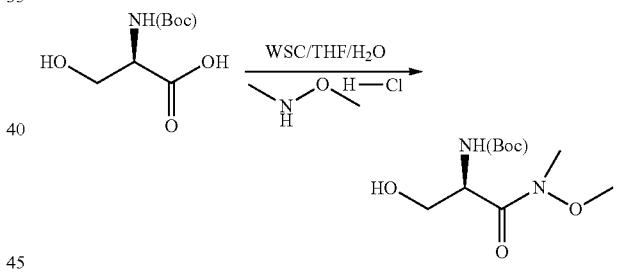

Boc-D-Serine (25.5 g, 124.5 mmol, 1.0 equiv.) was dissolved in tetrahydrofuran (112 mL) and N,O-dimethylhydroxylamine hydrochloride (14 g, 143.3 mmol, 1.2 equiv.) in water (112 mL) was added. While cooling in an ice bath, 1N sodium hydroxide was added to bring the pH to 4.5, then sodium hydroxide (2.45 g, 61.2 mmol, 0.5 equiv.) in water (329 mL) was added to maintain pH 4.5 and a solution of N-ethyl-N'-(3-dimethylaminopropyl)carbodiimide hydrochloride (27.8 g, 145.0 mmol, 1.2 equiv.) in water (281 mL) was slowly added during 30 min (the reaction was monitored by pH meter). After stirring for 20 h at r.t., the solution was saturated with sodium chloride and extracted 3× with ethyl acetate (201 mL). Combined organic extracts were concentrated to give a crude solid. The solid was dissolved in ethyl acetate with the help of the heating and hexanes were added to give a light orange solution. As the solution cooled, small colorless crystals started forming. The solution was allowed to stand at r.t. for 30 min before being placed in an ice-bath for 30 min. The resulting colorless crystals were filtered and rinsed with 10% ethyl acetate/hexanes and dried in air to afford the title compound as a shiny snowflakes like solid (16.48 g). The filtrate was concentrated and recrystallized to give the second crop (9.03 g) as a white solid. (total 25.5 g, 83%). $^1$HNMR (300 MHz, CDCl$_3$), δ 5.56 (brs, 1H), 4.80 (brs, 1H), 3.83-3.78 (m, 5H), 3.23 (s, 3H), 2.52 (brs, 1H), 1.45 (s, 9H).

Example 11: Synthesis of (R)-tert-butyl 4-(methoxy (methyl)carbamoyl)-2,2-dimethyloxazolidine-3-carboxylate

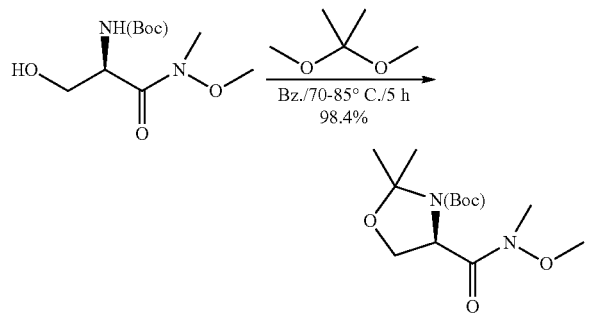

A suspension of (R)-tert-butyl (3-hydroxy-1-(methoxy (methyl)amino)-1-oxopropan-2-yl)carbamate (49 g, 197.4 mmol, 1.0 equiv.) in dry benzene (900 ml) was treated with 2,2-dimethoxypropane (200 ml, 1626.5 mmol, 8.2 equiv.) and pyridinium p-toluenesulfonate (5 g, 20.0 mmol, 0.1 equiv.) and a Dean-Stark trap was attached on a 2 L round bottom flask. The mixture was refluxed (75° C.) for 1 h without distillation and then the MeOH-benzene azeotrope was slowly distilled at 80° C. during 0.5 h (11 mL, $^1$HNMR indicated methanol and benzene and small amount of 2,2-dimethoxypropane), oil bath was then heated to 85° C. and stirred for total 5 h with distillation (200 mL). TLC (50% ethyl acetate/hexanes, KMnO$_4$ stained, R$_f$ of product, 0.52, starting material, 0.15) indicated the reaction was complete. After cooling, hexanes were added and the solution stored in a refrigerator overnight. The resulting solid was filtered off and saturated aq. NaHCO$_3$ was added. Extraction with ethyl acetate, followed by washing of the organic extracts with brine, drying over anhydrous sodium sulfate, filtering and concentration gave crude product as an oil to which was added hexanes and the resulting orange solid filtered off. The filtrate was concentrated to give white solid, which was filtered and rinsed with hexanes and dried in air to give the product (43 g). The white solid was dried in a vacuum oven for 2 h. The filtrate was concentrated and hexanes were added. The resulting solid was filtered and gave the second crop of the title product as a white solid. (total 56 g, 98%). LCMS: [M+1]$^+$5, 289.0. $^1$HNMR (300 Hz, DMSO-d6), δ 4.72-4.68 (m, 1H), 4.21-4.14 (m, 1H), 3.85-3.79 (m, 1H), 3.68-3.66 (m, 3H), 3.13-3.11 (m, 3H), 1.54 (s, 3H), 1.45-1.41 (m, 6H), 1.33 (s, 6H).

Example 12: Synthesis of (R)-tert-butyl 4-d$_3$-acetyl-2,2-dimethyloxazolidine-3-carboxylate

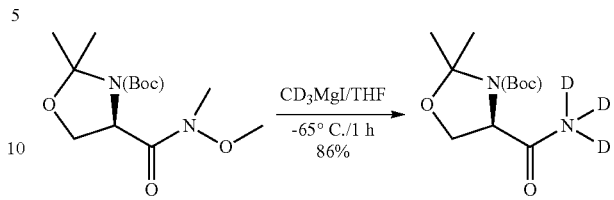

To a solution of (R)-tert-butyl 4-(methoxy(methyl)carbamoyl)-2,2-dimethyloxazolidine-3-carboxylate (22 g, 76.3 mmol, 1.0 equiv.) in dry tetrahydrofuran (63 mL) was added dropwise d$_3$-Methylmaginesium iodide (91 ml, 91.6 mmol, 1.2 equiv.) which had been transferred to a 100 mL dropping funnel under argon atmosphere via canula at r.t. within 15 min. After stirring at r.t. for 1 h, a small aliquot was quenched with saturated ammonium chloride solution at 0° C. TLC (50% ethyl acetate/hexanes) and LCMS indicated the starting material was all consumed. The reaction was cooled to 0° C. and quenched with saturated ammonium chloride solution and extracted with ethyl acetate (3×). The combined organics were washed with brine, dried over anhydrous sodium sulfate, filtered and concentrated to give a yellow oil. The crude material was dissolved in dichloromethane and loaded to a silica gel (120 g, 0-70% ethyl acetate/hexanes) to afford the title compound as a pale yellow oil (16.24 g, 86%). $^1$HNMR (300 MHz, DMSO-d6), δ 4.41 (dd, J=7.5, 3.0 Hz, 1H), 4.14-4.08 (m, 1H), 3.94 (dd, J=9.8, 2.5 Hz, 1H), 1.54 (s, 3H), 1.42 (s, 7H), 1.33 (s, 5H). (Ref: Journal of Medicinal Chemistry, 57(14), 5935-5948; 2014)

Example 13: Synthesis of (R,S)-tert-butyl 4-(2-hydroxypropan-2-yl-2-methyl-2-d$_3$-methyloxazolidine-3-carboxylate

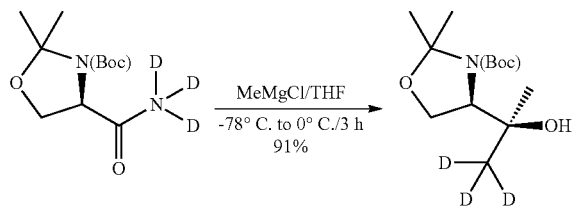

Methylmagnesiumchloride (50 ml, 150.4 mmol, 3.0 equiv.) in THF was added dropwise to a cooled solution of (R)-tert-butyl 4-d$_3$-acetyl-2,2-dimethyloxazolidine-3-carboxylate (12.4 g, 50.1 mmol, 1.0 equiv.) in tetrahydrofuran (60 mL) in a 500 mL round bottom flask at −78° C. via dropping funnel within 15 min. After 15 min, the temperature was allowed to rise slowly to 5° C. during 3 h. The mixture was cooled to 0° C. and quenched with saturated NH$_4$Cl, extracted with ethyl acetate and purified by chromatography. The crude light yellow oil was dissolved in dichloromethane and loaded to a silica gel column (120 g, 10-20% ethyl acetate/hexanes) to give pure product as a pale yellow oil (12.14 g, 91%). The methyl group from the two different isomers overlapped and the ratio of isomers could not be determined by $^1$H NMR. $^1$HNMR (300 MHz, CDCl$_3$), δ 5.26 (brs, 1H), 4.01-3.98 (m, 2H), 3.79 (brs, 1H), 1.59 (s, 3H), 1.50 (s, 12H), 1.18 (s, 3H).

Example 14: Synthesis of tert-butyl((2R,3S)-1,3-dihydroxy-3-d$_3$-methylbutan-2-yl)carbamate

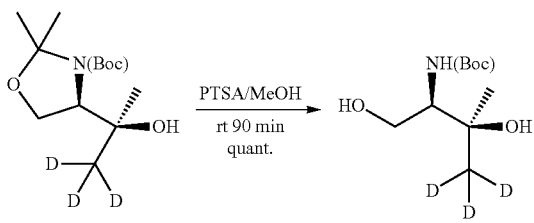

A solution of (R,S)-tert-butyl 4-(2-hydroxypropan-2-yl)-2-methyl-2-d$_3$-methyloxazolidine-3-carboxylate (12 g, 45.7 mmol, 1.0 equiv.) in methanol (405 mL) was treated with p-toluenesulfonic acid hydrate (0.87 g, 4.6 mmol, 0.1 equiv.). The solution was stirred for 70 min. at r.t. LCMS indicated presence of starting material and the reaction was allowed to continue to stir at r.t. for additional 30 min. TLC (20% ethyl acetate/hexanes) indicated all starting material was consumed and TLC (50% ethyl acetate/hexanes) shoed the desired product at R$_f$:0.6. The reaction was quenched with saturated aqueous NaHCO$_3$ at r.t. and concentrated in vacuo in order to remove most of the methanol. The concentrated mixture was diluted with saturated brine (and solid salt) and extracted with ethyl acetate (3×100 mL). The organic extracts were combined and dried over anhydrous sodium sulfate and concentrated to give pure product as a colorless oil. The oil was dissolved in DICHLOREMETHANE and loaded on a silica gel column (120 g, 0-100% ethyl acetate/hexanes) to afford the title compound as a clear oil (quant.). LCMS indicated desired mass [M+1]$^+$, 223.0. Ratio of two isomers:desired:undesired=2.61:1 by $^1$H NMR. $^1$HNMR (300 MHz, DMSO-d6), δ 6.21 (d, J=7.5 Hz, 1H), 4.42 (t, J=5.4 Hz, 1H), 4.31 (s, 1H), 3.66-3.62 (m, 1H), 1.38 (s, 9H), 0.97 (s, 3H).

Example 15: Synthesis of (2S,3S)-2-((tert-butoxycarbonyl)amino)-3-hydroxy-3-d$_3$-methylbutanoic acid

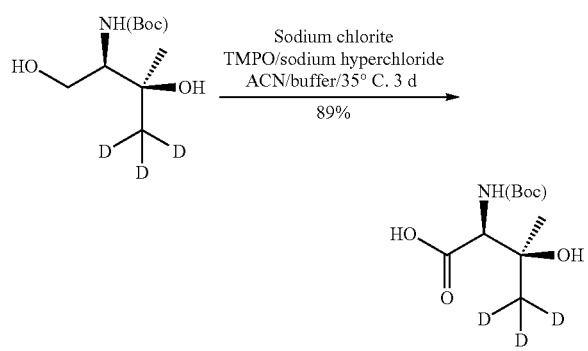

TEMPO (0.71 g, 4.5 mmol, 0.1 equiv.) was added to a mixture of tert-butyl ((2R,3S)-1,3-dihydroxy-3-d$_3$-methylbutan-2-yl)carbamate (10.1 g, 45.4 mmol, 1.0 equiv.) in acetonitrile (230 mL) and sodium phosphate buffer (182 ml, 127.3 mmol, 2.8 equiv.) and the resulting mixture was heated to 35° C. The mixture was then treated by simultaneous addition of 80.0% sodium chlorite (13 g, 116.1 mmol, 2.6 equiv.) solution in water (39 mL) and 4 drops of a very dilute sodium hypochlorite (3 mL of commercial solution in 100 mL of water). The mixture was stirred at 35° C. for 3 days, LCMS indicated the reaction was complete and the reaction was typically very dark. The reaction mixture was treated with citric acid (9.2 g, 47.8 mmol, 1.1 equiv.) (pH 3), saturated with sodium chloride and extracted with ethyl acetate (200 ml) (3×). The organic extracts were combined and concentrated. The resulting residue was dissolved into sodium carbonate solution 2M (307 ml) and the solution was extracted with ethyl acetate (2×). The aqueous layer was cooled to 0° C., the pH was adjusted to 3.0 using 4 M solution of H$_3$PO$_4$ (307 mL to pH 3) and the solution was saturated with sodium chloride (stirred at r.t. for 30 min). The resulting mixture was extracted with ethyl acetate (200 mL) (3×), the organic phases were combined, dried, filtered and concentrated under reduced pressure to give the title compound as a semi-solid which was sonicated with diethyl ether and filtered to give a white solid (9.59 g, 89%). The ratio of the two isomers was not be able to be determined by $^1$H NMR since the two methyl signals overlapped. $^1$HNMR (300 MHz, DMSO-d6), δ 6.51 (d, J=8.7 Hz, 1H), 4.65 (brs, 1H), 3.85 (d, J=9.6 Hz, 1H), 1.38 (s, 9H), 1.14 (s, 3H).

Example 16: Synthesis of tert-butyl((2S,3S)-1-((benzyloxy)amino)-3-hydroxy-3-d$_3$-methyl-1-oxobutan-2-yl)carbamate

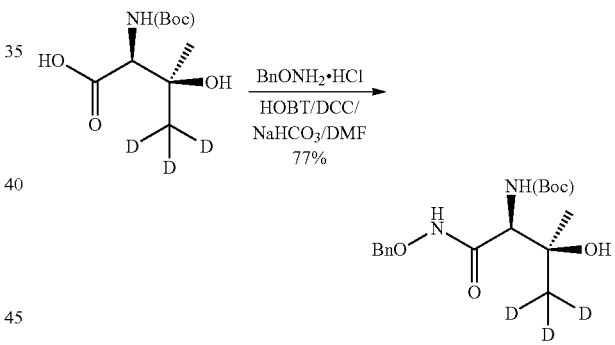

N,N'-dicyclohexylcarbodiimide (4.7 g, 23.0 mmol, 1.1 equiv.) was added to a solution of (2S,3S)-2-((tert-butoxycarbonyl)amino)-3-hydroxy-3-d$_3$-methylbutanoic acid (4.93 g, 20.9 mmol, 1.0 equiv.) in N,N-dimethylformamide (65 ml) at rt followed by 1-hydroxybenzotriazole (3.1 g, 23.0 mmol, 1.1 equiv.). The resulting mixture was stirred at rt for 30 min, and O-benzylhydroxylamine hydrochloride (3.66 g, 23.0 mmol, 1.1 equiv.) was added followed by sodium bicarbonate (7.0 g, 83.5 mmol, 4.0 equiv.). The reaction mixture was stirred at rt for 15 h. LCMS indicated the desired mass and the mass of (Z)—N-(((benzylamino)oxy)(cyclohexylamino)methylene)cyclohexanamine ([M+1]$^+$, 330). TLC (30% ethyl acetate/hexanes) indicated all starting carboxylic acid was consumed and the mixture was filtered through a Celite pad into a saturated sodium bicarbonate solution and washed with ethyl acetate (2×20 mL). The filtrate was diluted with ethyl acetate (500 mL) and washed with water (2×), brine, dried over anhydrous sodium sulfate, filtered and concentrated. The resulting residue was dissolved in dichloromethane and loaded to a silica gel column (80 g, 30-40% ethyl acetate/hexanes) to give the title compound as a colorless solid (5.48 g, 77%). The ratio of the two isomers was not be able to be determined by $^1$H NMR since the two methyl signals were overlapped. $^1$HNMR (300 MHz, DMSO-d6), δ 11.04 (s, 1H), 7.39-7.33 (m, 5H), 6.42 (d, J=9.3 Hz, 1H), 4.79 (s, 2H), 4.62 (s, 1H), 3.76 (d, J=9.6 Hz, 1H), 1.39 (s, 9H), 1.06 (s, 3H).

Example 17: Synthesis of tert-butyl((2R,3S)-1-(benzyloxy)-2-d$_3$-methyl-2-methyl-4-oxoazetidin-3-yl) carbamate

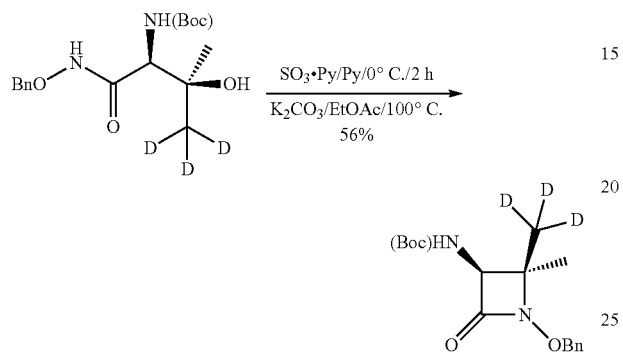

98.0% sulfur trioxide pyridine complex (4.6 g, 28.5 mmol, 2.0 equiv.) was added to a solution of tert-butyl ((2S,3S)-1-((benzyloxy)amino)-3-hydroxy-3-d$_3$-methyl-1-oxobutan-2-yl)carbamate (4.87 g, 14.3 mmol, 1.0 equiv.) in pyridine (48 mL) at 0° C. in portions, the ice-bath was removed and the mixture was stirred at r.t. for 4 h at which point the suspension became a clear solution. Crude $^1$H NMR indicated the reaction was complete. Pyridine was removed in vacuo and the residue was triturated with diethyl ether/hexanes (1:10, 50 mL) to remove the major portion of pyridine at 30° C. with the help of an oil pump. A solution of potassium carbonate (12 g, 87.8 mmol, 6.2 equiv.) in water (58 mL) and ethyl acetate (42 ml) were added to the solid intermediate. The resulting mixture was heated under reflux (100° C.) for 16 h. The ethyl acetate layer was separated, the aqueous layer was extracted with ethyl acetate (2×, total 160 mL) and the combined organic layers were washed with brine, dried over anhydrous sodium sulfate, filtered and concentrated. The resultant material was dissolved in dichloromethane and loaded on a silica gel column (80 g, 30-40% ethyl acetate/hexanes) to afford the title compound as a white powder (2.59 g, 56%). The ratio of two isomers:desired:undesired was 2.88:1 by $^1$H NMR. $^1$HNMR (300 MHz, DMSO-d6), δ 7.72 (d, J=9.0 Hz, 1H), 7.43-7.38 (m, 5H), 4.92 (s, 2H), 4.24 (d, J=8.7 Hz, 1H), 1.39 (s, 9H), 1.27 (s, 3H).

Example 18: Synthesis of tert-butyl((2R,3S)-2-d$_3$-methyl-1-hydroxy-2-methyl-4-oxoazetidin-3-yl)carbamate

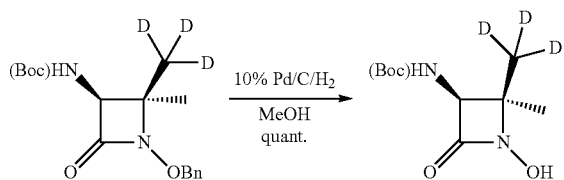

10.0% palladium on carbon (1.1 g, 1.0 mmol, 0.1 equiv.) (wet, ~50% water) was added to a solution of tert-butyl ((2R,3S)-1-(benzyloxy)-2-d$_3$-methyl-2-methyl-4-oxoazetidin-3-yecarbamate (3.29 g, 10.2 mmol, 1.0 equiv.) in methanol (63 mL) and the mixture was hydrogenated under balloon at r.t. for 12 h. TLC (30% ethyl acetate/hexanes, Rf 0.2, stained with KMnO$_4$) indicated the reaction was complete. The reaction was degassed and blanket with argon and filtered through a Celite pad which was rinsed with methanol (2×). The filtrate was concentrated in vacuo to give the title compound as a white solid (quant.). The ratio of two isomers:desired:undesired=2.49:1 by $^1$H NMR. $^1$HNMR (300 MHz, DMSO-d6), δ 7.68 (d, J=8.7 Hz, 1H), 4.19 (d, J=9.0 Hz, 1H), 1.39 (s, 9H), 1.28 (s, 3H).

Example 19: Synthesis of (2R,3S)-3-amino-2-d$_3$-methyl-2-methyl-4-oxoazetidin-1-yl hydrogen sulfate

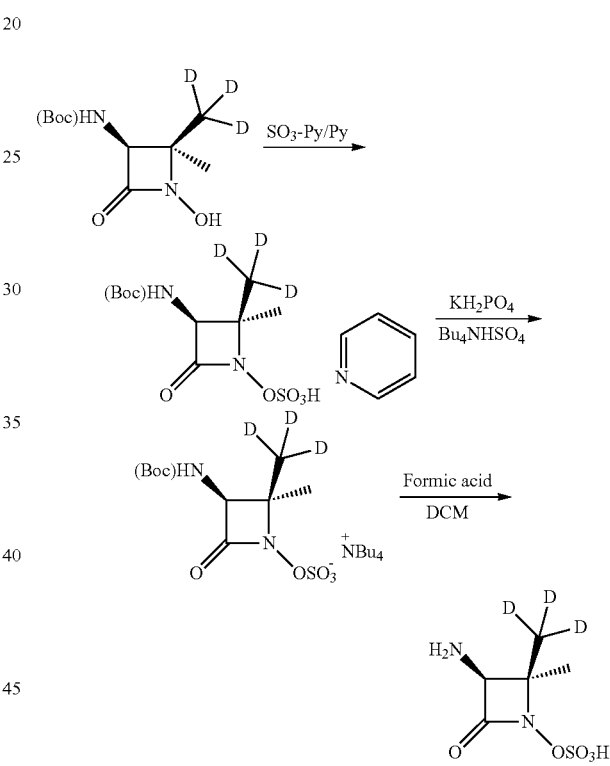

Sulfur trioxide pyridine complex (3.2 g, 20.3 mmol, 2.0 equiv.) was added to a solution of tert-butyl ((2R,3S)-2-d$_3$-methyl-1-hydroxy-2-methyl-4-oxoazetidin-3-yl)carbamate (2.4 g, 10.2 mmol, 1.0 equiv.) in pyridine (24 mL) at 0° C. The resulting mixture was stirred at rt for 1.5 h and concentrated in vacuo to give the title compound as a foam that is used directly next step.

Pyridinium (2R,3S)-3-((tert-butoxycarbonyl)amino)-2-d$_3$-methyl-2-methyl-4-oxoazetidin-1-yl hydrogen sulfate (4.0 g, 10.2 mmol, 1.0 equiv.) was dissolved in 0.5 M Potassium phosphate monobasic (13.9 g, 102.4 mmol, 10.1 equiv.) in water (199 mL) solution. The mixture was extracted with dichloromethane (2×10 mL). The aqueous layer was cooled to 0° C. and 98.0% tetrabutylammonium hydrogen sulfate (4.1 g, 11.8 mmol, 1.2 equiv.) was added to give a white suspension. The resulting mixture was stirred at 0-5° C. for 1 h and extracted with dichloromethane (5×50 mL). The combined dichloromethane layers were dried over anhydrous magnesium sulfate, filtered and concentrated in vacuo to give the title compound which was used directly without purification.

Tetrabutylammonium (2R,3S)-3-((tert-butoxycarbonyl)amino)-2-d₃-methyl-2-methyl-4-oxoazetidin-1-yl hydrogen sulfate (5.86 g, 10.6 mmol, 1.0 equiv.) was dissolved in formic acid (15 mL) and the resulting solution was stirred at r.t. for 2 days to provide white precipitate. The mixture was added dichloromethane and cooled to 0° C. and the resulting solid was filtered and dried in air for 10 min to afford the title compound as a white powder (1.35 g, 60% over three steps). The ratio of the two isomers was not be able to be determined since the two methyl signals were overlapped. ¹HNMR (300 MHz, DMSO-d6), δ 8.70 (brs, 2H), 4.15 (s, 1H), 1.42 (s, 3H).

Example 20: Synthesis of tert-butyl 2-(((Z)-(2-(((2R,3S)-2-d₃-Methyl-2-methyl-4-oxo-1-(sulfooxy)azetidin-3-ylamino)-2-oxo-1-(2-(tritylamino)thiazol-4-yl)ethylidene)amino)oxy)acetate

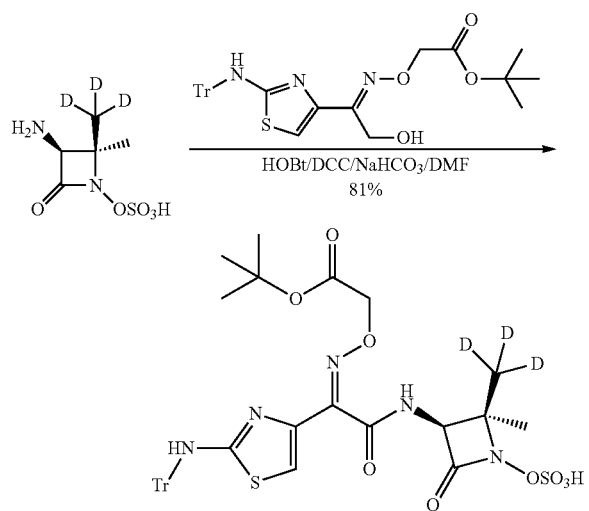

N,N'-dicyclohexylcarbodiimide (0.426 g, 2.1 mmol, 1.1 equiv.) was added to a solution of (Z)-2-((2-(tert-butoxy)-2-oxoethoxy)imino)-2-(2-(tritylamino)thiazol-4-yl)acetic acid (1.122 g, 2.1 mmol, 1.1 equiv.) in N,N-dimethylformamide (14 mL) at r.t. followed by 1-hydroxybenzotriazole (0.28 g, 2.1 mmol, 1.1 equiv.). The resulting mixture was stirred at r.t. for 30 min, and (2R,3S)-3-amino-2-d₃-methyl-2-methyl-4-oxoazetidin-1-yl hydrogen sulfate (0.4 g, 1.9 mmol, 1.0 equiv.) was added followed by sodium bicarbonate (0.63 g, 7.5 mmol, 4.0 equiv.). The resulting mixture was stirred at rt overnight and concentrated in vacuo at 30° C. to dryness. The residue was dissolved in dichloromethane and loaded to a silica gel column (12 g, 5-10% MeOH/dichloromethane) to afford the title compound (1.12 g, 81%) which contains dichloromethane residue and small amount of impurities. The ratio of two isomers was not be able to be determined since one of the methyl signal was overlapped with tert-butyl signal by ¹H NMR. ¹HNMR (300 MHz, DMSO-d6), δ 9.33 (d, J=7.5 Hz, 1H), 8.84 (s, 1H), 7.36-7.20 (m, 15H), 6.71 (s, 1H), 4.54-4.50 (m, 3H), 1.42-1.40 (m, 12H).

Example 21: Synthesis of 2-(((Z)-(1-(2-aminothiazol-4-yl)-2-(((2R,3S)-2-d₃-2-methyl-4-oxo-1-(sulfooxy)azetidin-3-ylamino)-2-oxoethylidene)amino)oxy)acetic acid

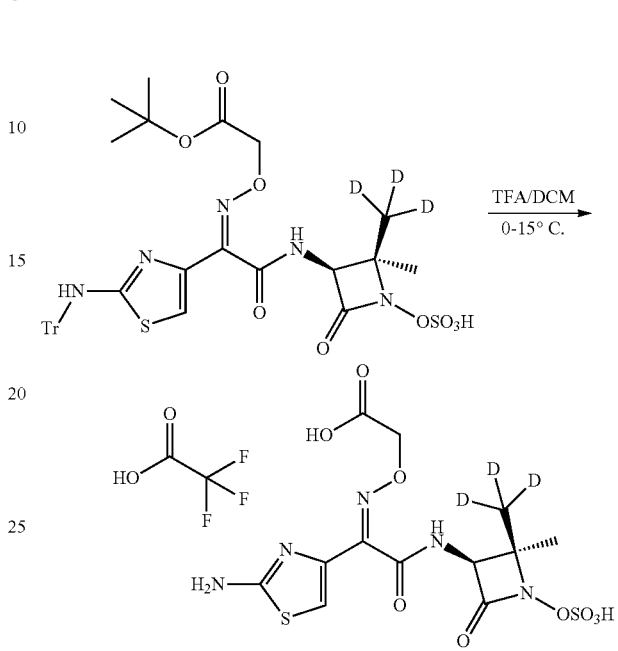

Tert-butyl 2-(((Z)-2-(((2R,3S)-2-d₃-methyl-2-methyl-4-oxo-1-(sulfooxy)azetidin-3-yl)amino)-2-oxo-1-(2-(tritylamino)thiazol-4-yl)ethylidene)amino)oxy)acetate (1.1 g, 1.5 mmol, 1.0 equiv.) and anisole (32 ul, 0.3 mmol, 0.2 equiv.) and dry dichloromethane (6 mL) were charged in a flask with a stir bar under argon. The suspension was cooled to 0° C. and trifluoroacetic acid (6 ml, 80.8 mmol, 54.3 equiv.) was added dropwise within 7 min. The suspension became yellow once TFA was added. The ice-bath was allowed to warm to up to 10° C. within 4 h, LCMS indicated desired mass at retention time 3.89 min. The reaction was cooled to 0° C. with ice-bath and cold deionized water (12 mL) was added dropwise. After separation, the aqueous layer was lyophilized in a 250 mL round bottom flask overnight. The resulting yellow material was added to dichloromethane and acetonitrile and sonicated. The white solid was filtered and transferred into a 20 mL vial with the help of water and acetonitrile and lyophilized overnight to afford a white fluffy solid (488 mg, 74%). LCMS: [M+1]⁺, 441.1.

Example 22: Removal of TFA

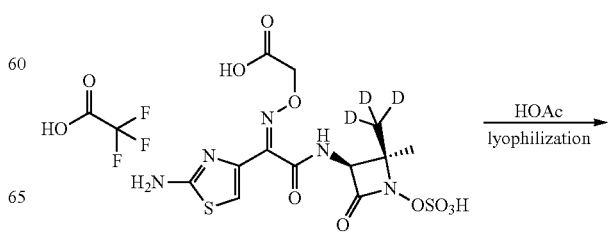

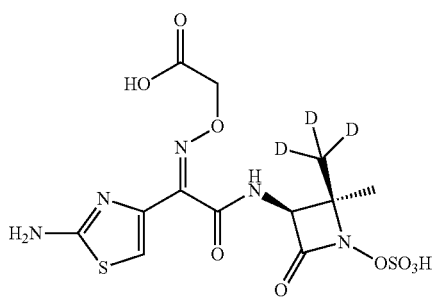

2-(((Z)-(1-(2-aminothiazol-4-yl)-2-(((2R,3S)-2-d$_3$-2-methyl-4-oxo-1-(sulfooxy)azetidin-3-yl)amino)-2-oxoethylidene)amino)oxy)acetic acid (unspecified amount) was dissolved in D$_2$O (700 uL) and acetic acid (4 ml) (1 mL×4) and the resulting clear solution was stirred at 0° C. for 30 min. The pale yellow clear solution was lyophilized overnight. The process was repeated six times to afford the final product (44 mg, 88%). TFA 2.9% by weight after six cycles. Acetic acid content is ~1% by weight (7% mol). The ratio between the desired and undesired isomers: 2.66:1 by $^1$H NMR. $^1$HNMR (300 MHz, D$_2$O), δ 7.01 (s, 1H), 4.82 (s, 1H), 4.67 (s, 2H, overlapped with water), 1.47 (s, 3H). $^{19}$FNMR (282 MHz, D$_2$O), δ −75.69. LCMS: [M+1]$^+$, 441.3.

Example 23: Synthesis of (R)-tert-butyl 4-acetyl-2,2-dimethyloxazolidine-3-carboxylate

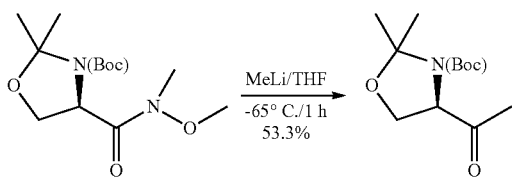

A solution of (R)-tert-butyl 4-(methoxy(methyl)carbamoyl)-2,2-dimethyloxazolidine-3-carboxylate (16.2 g, 56.0 mmol, 1.0 equiv.) in dry tetrahydrofuran (46 mL) was cooled to −63° C., and slowly treated with a 1.6 M methyllithium solution in diethyl ether (70 mL). After stirring at −60° C. for 4 h, a small aliquot was quenched with saturated ammonium chloride solution at −20° C., LCMS indicated desired mass along with starting material. TLC (50% ethyl acetate/hexanes, KMnO$_4$ stained showed three spots: R$_f$, starting material 0.125, product: 0.5, 0.75). The reaction mixture was cooled to −40° C. and quenched with saturated ammonium chloride slowly and allowed to warm to rt and extracted with diethyl ether (1×) and ethyl acetate (2×). Combined organic layers were washed with brine, dried over anhydrous sodium sulfate, filtered and concentrated to give a yellow oil (13.41 g). The crude material was dissolved in dichloromethane and loaded on a silica gel column (120 g, 0-100% ethyl acetate/hexanes) to give the desired product as a pale yellow oil (7.29 g, 53.3%). $^1$HNMR (300 MHz, DMSO-d6), δ 4.41 (dd, J=7.5, 3.0 Hz, 1H), 4.15-4.08 (m, 1H), 3.94 (dd, J=9.6, 2.7 Hz, 1H), 2.12 (s, 3H), 1.54 (s, 3H), 1.42-1.41 (m, 6H), 1.33 (s, 6H).

Example 24: Synthesis of (R,R)-tert-butyl 4-(2-hydroxypropan-2-yl)-2-methyl-2-d$_3$-methyloxazolidine-3-carboxylate

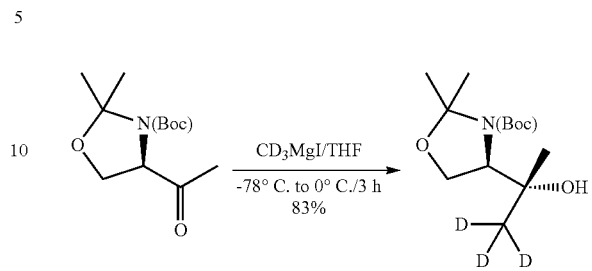

1 M solution of d$_3$-Methylmagnesium iodide (82 ml, 82.0 mmol, 2.8 equiv.) in diethyl ether was added dropwise to a cooled solution of (R)-tert-butyl 4-acetyl-2,2-dimethyloxazolidine-3-carboxylate (7.3 g, 29.8 mmol, 1.0 equiv.) in tetrahydrofuran (37 mL) in a 250 mL round bottom flask at −78° C., which resulted in formation of a white precipitate. After 15 min, the temperature was allowed to rise slowly to 0° C. during 3 h. The mixture was cooled to −60° C., quenched with saturated NH$_4$Cl, extracted with Et$_2$O and purified by chromatography (ethyl acetate/hexanes: 10%-20%) to give as pure product a pale yellow oil (6.46 g, 83%). The ratio of two isomers was not able to be determined since methyl signal and tert-butyl signal overlapped. $^1$HNMR (300 MHz, CDCl$_3$), δ 4.70-4.50 (brs, 1H), 4.04-3.99 (m, 1H), 3.87-3.70 (m, 2H), 1.50 (s, 3H), 1.42 (s, 12H), 1.07-1.02 (d, J=15.3 Hz, 3H).

Example 25: Synthesis of tert-butyl((2R,3R)-1,3-dihydroxy-3-methylbutan-2-yl)carbamate

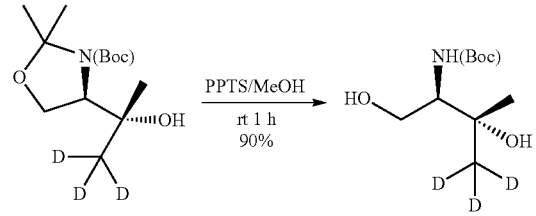

A solution of (R,R)-tert-butyl 4-(2-hydroxypropan-2-yl)-2-methyl-2-d$_3$-methyloxazolidine-3-carboxylate (6.4 g, 24.4 mmol, 1.0 equiv.) in methanol (216 mL) was treated with p-toluenesulfonic acid hydrate (0.46 g, 2.4 mmol, 0.1 equiv.). The solution was stirred for 100 min. at rt. The reaction was quenched with saturated aq. NaHCO$_3$ at rt, and concentrated in vacuo in order to remove most methanol. The concentrated mixture was diluted with saturated brine (and solid salt) and extracted with ethyl acetate (3×100 mL). The organic extracts were combined and dried over anhydrous sodium sulfate, concentrated to give as a colorless oil (4.89 g, 90%). LCMS: [M+1]$^+$, 223.0. The ratio between the desired and undesired isomers: 4.82:1 by $^1$H NMR. $^1$HNMR (300 MHz, CDCl$_3$), δ 5.63 (m, 1H), 4.05-4.01 (m, 1H), 3.83-3.78 (m, 1H), 3.45 (m, 1H), 2.62-2.55 (m, 2H), 1.45 (s, 9H), 1.35 (s, 3H).

Example 26: Synthesis of (2S,3R)-2-((tert-butoxycarbonyl)amino)-3-hydroxy-3-methylbutanoic acid

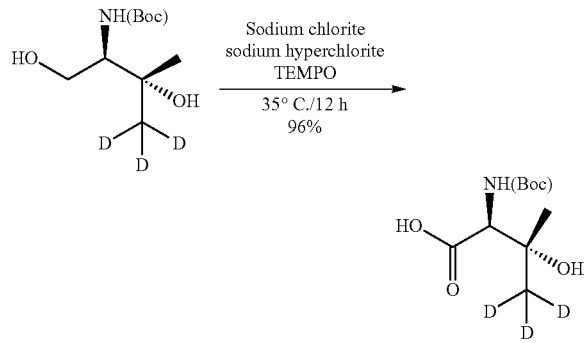

TEMPO (0.35 g, 2.2 mmol, 0.1 equiv.) was added to a mixture of tert-butyl ((2R,3R)-1,3-dihydroxy-3-methylbutan-2-yl)carbamate (4.89 g, 22.0 mmol, 1.0 equiv.) in acetonitrile (111 mL) and sodium phosphate buffer (88 mL) and the resulting mixture was heated to 35° C. The mixture was then treated by simultaneous addition of 80.0% sodium chlorite (6.4 g, 56.2 mmol, 2.5 equiv.) solution in water (18 mL) and 4 drops of a very dilute sodium hypochlorite (3 mL of commercial solution in 100 mL of water). The mixture was stirred at 35° C. overnight, and LCMS indicated there was no reaction. TEMPO (0.35 g, 2.2 mmol, 0.1 equiv.) and sodium hypochlorite (0.44 ml, 7.1 mmol, 0.3 equiv.) was added and the reaction was allowed to stir at 35° C. for additional 8 h. LCMS indicated the reaction was incomplete with mostly starting material. The reaction was allowed to stir at 35° C. for additional 20 h and then r.t. for another day. LCMS indicated the reaction was complete and the reaction mixture was dark colored. The reaction mixture was treated with citric acid (4.44 g, 23.1 mmol, 1.0 equiv.) (pH 3), saturated with sodium chloride and extracted with ethyl acetate (130 ml) (3×). The organic extracts were combined and concentrated. The resulting residue was dissolved into sodium carbonate solution 2M (220 ml, 440.1 mmol, 19.7 equiv.) and the solution was extracted with ethyl acetate (2×). The aqueous layer was cooled to 0° C., the pH was adjusted to 3.0 using 4 M solution of H$_3$PO$_4$ (220 mL to pH 3) and the solution was saturated with sodium chloride (stirred at rt for 30 min). The resulting mixture was extracted with ethyl acetate (130 ml) (3×), the organic phases were combined, dried, filtered and concentrated under reduced pressure to give the title compound as a semi-solid which was triturated with diethyl ether to give a white solid (5 g, 96%). The ratio of two isomers was not able to be determined by $^1$H NMR since two methyl signals overlapped. $^1$HNMR (300 MHz, DMSO-d6), δ 6.51 (d, J=8.7 Hz, 1H), 3.85 (d, J=9.0 Hz, 1H), 1.39 (s, 9H), 1.16 (s, 3H).

Example 27: Synthesis of tert-butyl((2S,3R)-1-((benzyloxy)amino)-3-hydroxy-d$_3$-methyl-1-oxopentan-2-yl)carbamate

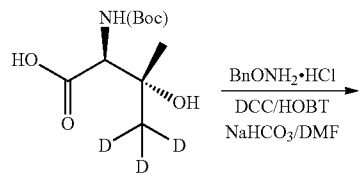

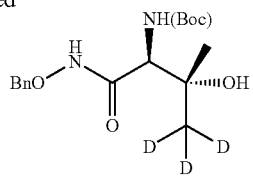

N,N'-dicyclohexylcarbodiimide (4.6 g, 22.1 mmol, 1.1 equiv.) was added to a solution of (2S,3R)-2-((tert-butoxycarbonyl)amino)-3-hydroxy-3-methylbutanoic acid (4.68 g, 19.8 mmol, 1.0 equiv.) in N,N-dimethylformamide (62 mL) at r.t. followed by 1-hydroxybenzotriazole (2.98 g, 22.1 mmol, 1.1 equiv.). The resulting mixture was stirred at rt for 30 min, and O-benzylhydroxylamine hydrochloride (3.6 g, 22.3 mmol, 1.1 equiv.) was added followed by sodium bicarbonate (6.7 g, 80.3 mmol, 4.0 equiv.). The reaction mixture was stirred at rt for 15 h. LCMS indicated the desired mass and the mass of (Z)—N-(((benzylamino)oxy)(cyclohexylamino)methylene)cyclohexanamine ([M+1]$^+$, 330. TLC (30% EA/Hex) indicated all starting carboxylic acid was consumed and the mixture was filtered through a Celite pad into a saturated sodium bicarbonate solution, washed with ethyl acetate (2×20 mL), the filtrate was diluted with ethyl acetate (200 mL) and washed with water (2×), brine, dried over anhydrous sodium sulfate, filtered and concentrated and co-evaporated with toluene. The resulting residue was dissolved in dichloromethane and loaded to a silica gel column (80 g, 30-40% ethyl acetate/hexanes) to give the title compound as a colorless solid (3.48 g, 51%). The ratio of two isomers was not able to be determined by $^1$H NMR since two methyl signals overlapped. $^1$HNMR (300 MHz, DMSO-d6), δ 11.04 (s, 1H), 7.39-7.35 (m, 5H), 6.42 (d, J=8.7 Hz, 1H), 4.79 (s, 2H), 4.62 (s, 1H), 3.76 (d, J=9.3 Hz, 1H), 1.39 (s, 9H), 1.09 (s, 3H).

Example 28: Synthesis of tert-butyl((2S,3S)-1-(benzyloxy)-2-d$_3$-methyl-2-methyl-4-oxoazetidin-3-yl)carbamate

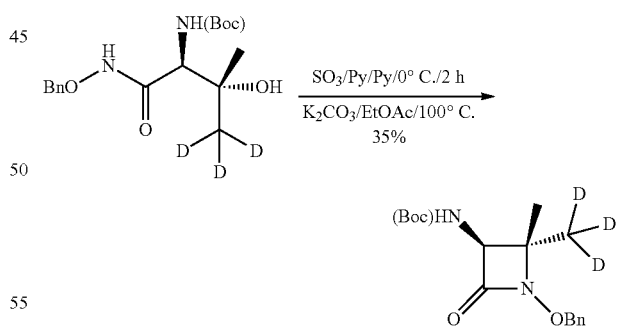

Sulfur trioxide pyridine complex (2.3 g, 14.4 mmol, 1.4 equiv.) was added to a solution of tert-butyl ((2S,3R)-1-((benzyloxy)amino)-3-hydroxy-3-d$_3$-methyl-1-oxobutan-2-yl)carbamate (3.48 g, 10.2 mmol, 1.0 equiv.) in pyridine (35 mL) at 0° C. in portions and the mixture was stirred for 2 h. Pyridine was removed in vacuo and the residue was triturated with diethyl ether/hexanes (1:10, 50 mL) to remove the major portion of the pyridine. A solution of potassium carbonate (8.7 g, 62.7 mmol, 6.1 equiv.) in water (42 mL) and ethyl acetate (30 ml) were added to the solid intermediate. The resulting mixture was heated under reflux (95° C. oil bath) for 6 h. The ethyl acetate layer was separated and the aqueous layer was extracted with ethyl acetate (2×, total 160 mL) and the combined organic layers were washed with brine, dried over anhydrous sodium sulfate, filtered and concentrated. The crude material was dissolved in dichloromethane and loaded on a silica gel column (40 g, 30-40% ethyl acetate/hexanes) to afford the title compound as a white powder (1.14 g, 35%). The ratio between the desired and undesired isomers: 4.25:1 by $^1$H NMR. $^1$HNMR (300 MHz, DMSO-d6), δ 7.72 (d, J=9.0 Hz, 1H), 7.41-7.39 (m, 5H), 4.92 (s, 2H), 4.24 (d, J=8.7 Hz, 1H), 1.39 (s, 9H), 1.27 (s, 0.61H), 1.05 (s, 2.59H).

Example 29: Synthesis of tert-butyl((2S,3S)-2-d$_3$-methyl-1-hydroxy-2-methyl-4-oxoazetidin-3-yl)carbamate

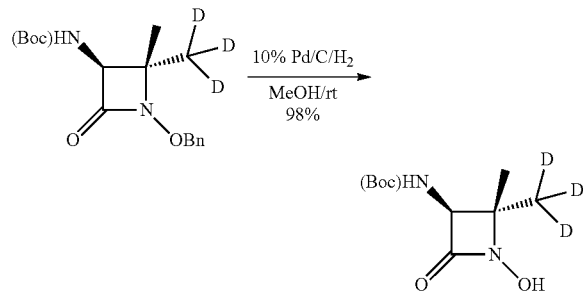

10.0% palladium on carbon (0.38 g, 0.4 mmol, 0.1 equiv.) (wet, ~50% water) was added to a solution of tert-butyl ((2S,3S)-1-(benzyloxy)-2-d$_3$-methyl-2-methyl-4-oxoazetidin-3-yecarbamate (1.140 g, 3.5 mmol, 1.0 equiv.) in methanol (22 mL) and the mixture was hydrogenated under balloon for 12 h. TLC (30% ethyl acetate/hexanes, Rf 0.2, stained with KMnO$_4$) indicated the reaction was complete. The reaction was degassed, blanketed with argon and filtered through a Celite pad which was rinsed with methanol (2×). The filtrate was concentrated in vacuo to give the title compound as a white solid (0.81 g, 98%). The ratio between the desired and undesired isomers: 4.45:1 by $^1$H NMR. $^1$HNMR (300 MHz, DMSO-d6), δ 9.98 (brs, 1H), 7.68 (d, J=8.1 Hz, 1H), 4.19 (d, J=9.0 Hz, 1H), 1.39 (s, 9H), 1.10 (s, 3H).

Example 30: Synthesis of (2S,3S)-3-amino-2-d$_3$-methyl-2-methyl-4-oxoazetidin-1-yl hydrogen sulfate

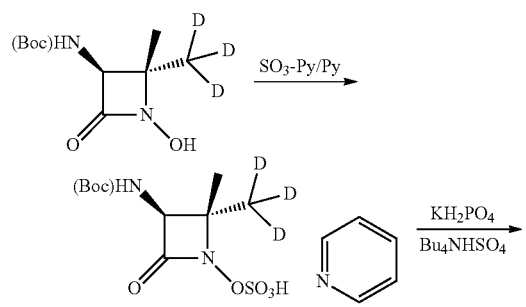

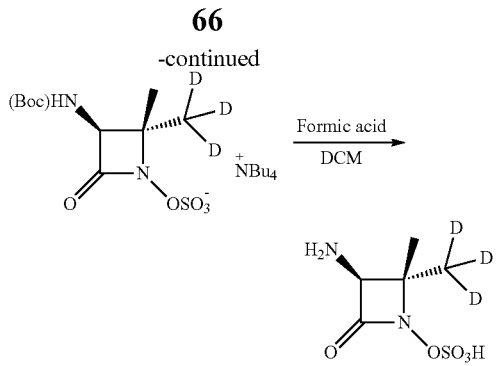

Sulfur trioxide pyridine complex (0.67 g, 4.2 mmol, 1.2 equiv.) was added to a solution of tert-butyl ((2S,3S)-2-d$_3$-methyl-1-hydroxy-2-methyl-4-oxoazetidin-3-yl)carbamate (0.81 g, 3.5 mmol, 1.0 equiv.) in pyridine (8 mL) at 0° C. The resulting mixture was stirred at rt for 1.5 h and concentrated in vacuo to give the title compound as a foam that is used directly next step.

Pyridinium (2S,3S)-3-((tert-butoxycarbonyl)amino)-2-d$_3$-methyl-2-methyl-4-oxoazetidin-1-yl sulfate (1.36 g, 3.5 mmol, 1.0 equiv.) was dissolved in 0.5 M potassium phosphate monobasic (4.8 g, 34.9 mmol, 10.0 equiv.) in water (68 ml) solution. The mixture was extracted with dichloromethane (2×10 mL). The aqueous layer was cooled to 0° C. and 98.0% tetrabutylammonium hydrogen sulfate (1.4 g, 4.0 mmol, 1.1 equiv.) was added to give a white suspension. The resulting mixture was stirred at 0-5° C. for 1 h and extracted with dichloromethane (5×50 mL). The combined dichloromethane layers were dried over anhydrous magnesium sulfate, filtered and concentrated in vacuo to give the title compound which was used directly without purification.

(2S,3S)-3-((tert-butoxycarbonyl)amino)-2-d$_3$-methyl-2-methyl-4-oxoazetidin-1-yl hydrogen sulfate (1.9 g, 6.1 mmol, 1.0 equiv.) was dissolved in formic acid (5 mL) and the resulting solution was stirred at r.t. for 5 h. No white precipitate formed. The mixture was added to dichloromethane, which resulted in formation of a white precipitate, and was stored at −20° C. for two days. The resulting solid was filtered but the solid blocked the filter paper and hexanes were added and semi-solid was dissolved in methanol and concentrated. The resulting solid was triturated with dichloromethane and dried under vacuum for 1 h and rinsed with cold dichloromethane to afford the title compound as a white solid (107 mg, 33%). The ratio of two isomers was not able to be determined since two methyl signals overlapped by $^1$H NMR. $^1$HNMR (300 MHz, DMSO-d6), δ 8.69 (brs, 2H), 4.17 (s, 1H), 1.41 (s, 3H).

Example 31: Synthesis of tert-butyl 2-(((Z)-(2-(((2S,3S)-2-d$_3$-methyl-2-methyl-4-oxo-1-(sulfooxy)azetidin-3-ylamino)-2-oxo-1-(2-(tritylamino)thiazol-4-yl)ethylidene)amino)oxy)acetate

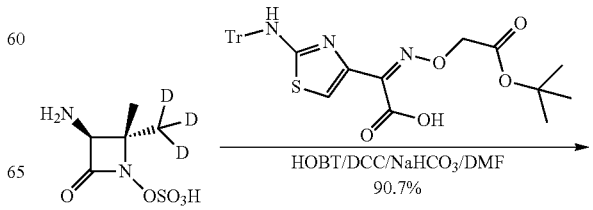

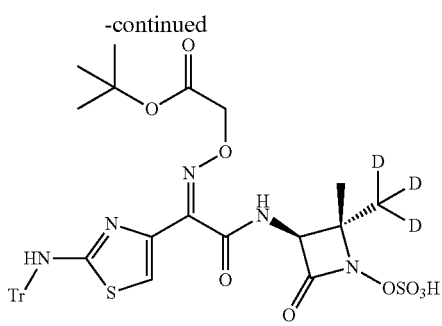

N,N'-dicyclohexylcarbodiimide (0.06 g, 0.3 mmol, 1.1 equiv.) was added to a solution of (Z)-2-((2-(tert-butoxy)-2-oxoethoxy)imino)-2-(2-(tritylamino)thiazol-4-yl)aceticacid (0.157 g, 0.3 mmol, 1.1 equiv.) in N,N-dimethylformamide (1.9 ml) at r.t. followed by 1-hydroxybenzotriazole (0.04 g, 0.3 mmol, 1.1 equiv.). The resulting mixture was stirred at rt for 30 min, and (2S,3S)-3-amino-2-$d_3$-methyl-2-methyl-4-oxoazetidin-1-yl hydrogen sulfate (0.056 g, 0.3 mmol, 1.0 equiv.) was added followed by sodium bicarbonate (0.088 g, 1.1 mmol, 4.0 equiv.). The resulting mixture was stirred at rt overnight and concentrated in vacuo at 30° C. (triturated with methanol, dichloromethane) to dryness. The residue was dissolved in dichloromethane and loaded to a silica gel column (12 g, 5-10% MeOH/dichloromethane) to afford the title compound as a white solid (176 mg, 90.7%). The ratio of two isomers was not able to be determined by $^1$H NMR since the two methyl signals overlapped. $^1$HNMR (300 MHz, DMSO-d6), δ 9.32 (d, J=7.5 Hz, 1H), 8.84 (s, 1H), 7.36-7.20 (m, 15H), 6.71 (s, 1H), 4.54-4.50 (m, 3H), 1.42 (s, 9H), 1.20 (s, 3H).

Example 32: Synthesis of 2-(((Z)-(1-(2-aminothiazol-4-yl-2-(((2S,3S)-2-($d_3$-methyl-2-methyl-4-oxo-1-(sulfooxy)azetidin-3-ylamino)-2-oxoethylidene)amino)oxy)acetic acid TFA salt

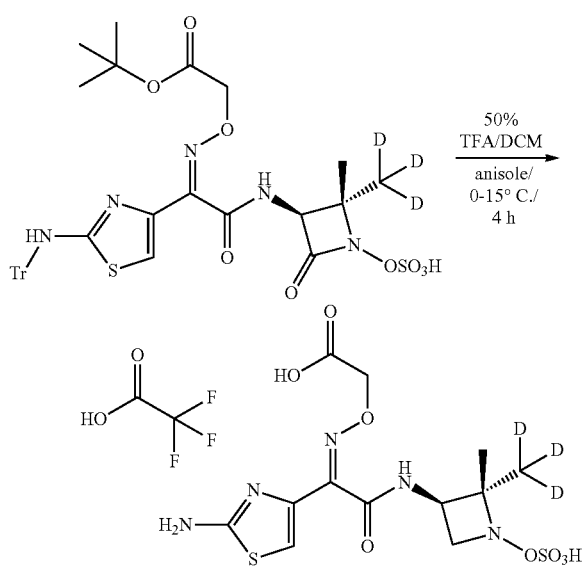

tert-Butyl 2-(((Z)-(2-(((2S,3S)-2-$d_3$-methyl-2-methyl-4-oxo-1-(sulfooxy)azetidin-3-yl)amino)-2-oxo-1-(2-(tritylamino)thiazol-4-yl)ethylidene)amino)oxy)acetate (0.176 g, 0.2 mmol, 1.0 equiv.) and anisole (6 ul, 0.1 mmol, 0.2 equiv.) and dry dichloromethane (1 mL) were charged into a flask with a stir bar under argon. The suspension was cooled to 0° C. and trifluoroacetic acid (1 ml, 13.5 mmol, 56.5 equiv.) was added dropwise within 5 min. The suspension became yellow once TFA was added. The ice-bath was allowed to warm to up to 15° C. within 4 h. LCMS indicated desired mass as m/z 441. The reaction was cooled to 0° C. with ice-bath and cold deionized water (2 mL) was added dropwise. After separation, aqueous layer was lyophilized in a 25 mL round bottom flask for 3 days. The resulting yellow material was added DCM and acetonitrile and sonicated. The white solid was filtered and all material was transferred into a 20 mL vial with the help of water and acetonitrile and lyophilized again to afford a white fluffy solid (90 mg, 68%). LCMS: [M+1]$^+$, 441.1.

Example 33: Removal of TFA

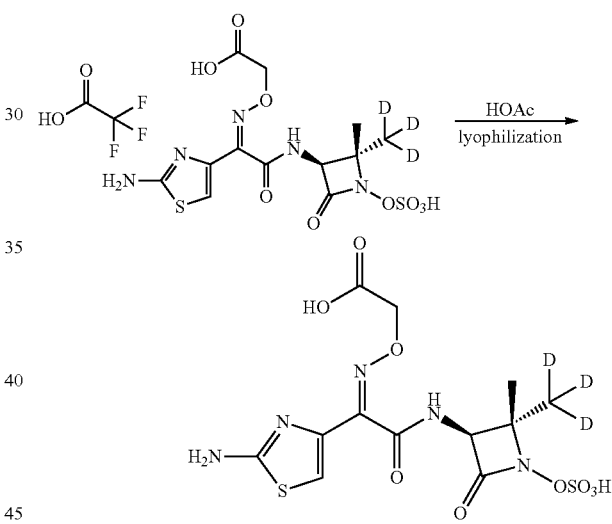

2-(((Z)-(1-(2-aminothiazol-4-yl)-2-(((2S,3S)-2-($d_3$-methyl-2-methyl-4-oxo-1-(sulfooxy)azetidin-3-yl)amino)-2-oxoethylidene)amino)oxy)acetic acid (25 mg) was dissolved in D$_2$O (650 uL) and analyzed by $^1$H NMR and $^{19}$F NMR with TFE (3 uL) and then transferred to a 20 mL vial and cooled to 0° C. and glacial acetic acid (1 mL) was added. The resulting solution was stirred at 0° C. for 30 min. The resulting mixture was lyophilized overnight, the process was repeated eight times to afford the title compound (21.5 mg, 86%). TFA 3.7% by weight and acetic acid content was barely visible by $^1$H NMR. The ratio between the desired and undesired isomers: 4.98:1 by $^1$H NMR. $^1$HNMR (300 MHz, D$_2$O), δ 7.07 (s, 1H), 4.89 (s, 1H), 4.70 (s, 2H, overlapped with water), 1.35 (s, 3H). $^{19}$FNMR (282 MHz, D$_2$O), δ −75.55.

Example 34: Synthesis of (Z)-2-((2-(tert-butoxy)-2-oxoethoxy)imino)-2-(2-(tritylamino)thiazol-4-yl)acetic acid

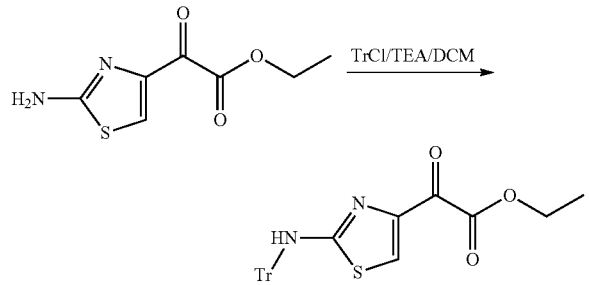

Triethylamine (4.03 ml, 28.9 mmol, 1.2 equiv.) and triphenylmethyl chloride (7.92 g, 28.4 mmol, 1.2 equiv.) were added to a suspension of 98.0% ethyl 2-(2-aminothiazol-4-yl)glyoxylate (5.0 g, 24.5 mmol, 1.0 equiv.) in dichloromethane (100 mL) at 0° C. The reaction mixture was stirred for 15 min. and then allowed to warm to ambient temperature over 3 h before the solvent was evaporated in vacuo. Water (100 mL) was added and was extracted with ethyl acetate. The organic layer was washed with brine, dried over anhydrous sodium sulfate and concentrated under reduced pressure. The crude material was purified by flash silica chromatography (80 g, 0-40% ethyl acetate/hexanes) to give a yellow solid (10 g, 92.3%). LCMS: [M+1]+, 442.7. ¹HNMR (300 MHz, DMSO-d6), δ 9.05 (s, 1H), 7.85 (s, 1H), 7.37-7.16 (m, 15H), 4.07-3.99 (m, 2H), 1.18-1.10 (m, 3H).

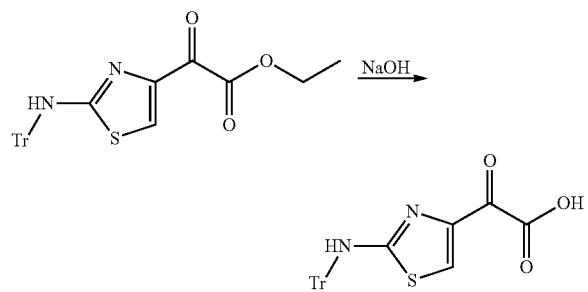

Sodium hydroxide (37 mL of a 1.0 N solution in water) was added to a solution of ethyl 2-(2-(tritylamino)thiazol-5-yl)acrylate (10.000 g, 22.6 mmol, 1.0 equiv.) in ethanol (90 mL) at 0° C. Tetrahydrofuran (25 mL) was added and the reaction was allowed to warm to ambient temperature over 3 h before the solvent was evaporated in vacuo. The resulting residue was acidified with aq. hydrochloric acid (6.0 N) to pH 2 and the product collected by suction filtration to yield a yellow solid (9.03 g, 96.4%). ¹HNMR (300 MHz, DMSO-d6), δ 8.99 (s, 1H), 7.74 (s, 1H), 7.33-7.20 (m, 15H).

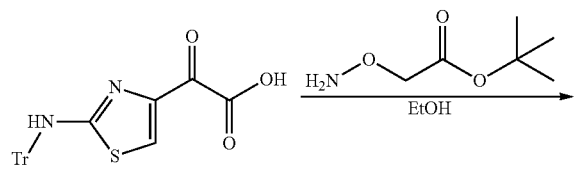

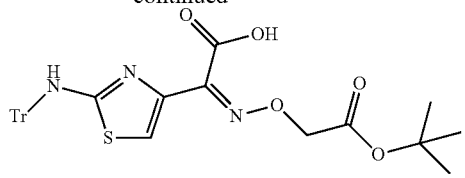

A solution of 98.0% tert-butyl 2-(aminooxy)acetate (3.27 g, 21.8 mmol, 1.0 equiv.) in methanol (100 mL) was treated with 2-oxo-2-(2-(tritylamino)thiazol-5-yl)acetic acid (9.03 g, 21.8 mmol, 1.0 equiv.) and stirred at ambient temperature for 3 h. The reaction mixture was evaporated in vacuo. The crude material was purified by flash silica chromatography (0-15% MeOH/dichloromethane, 120 g) to give a beige solid (9.33 g). HPLC analysis, indicated that there were two peaks (one major and the other one is minor) next to each other and not separable by flash column chromatography. Purified by prep-TLC (5% MeOH/DCM), the minor peak was isolated and concentrated. LCMS indicated the minor peak compound was the isomer of the major peak. The beige solid was recrystallized in methanol to give the desired compound as a white powder (8.22 g, 69.4%). LCMS: [M+1]+, 554.0. ¹HNMR (300 MHz, DMSO-d6), δ 8.82 (s, 1H), 7.33-7.17 (m, 15H), 6.82 (s, 1H), 4.51 (s, 2H), 1.39 (s, 9H).

Example 35: IV Dosing of Tigemonam and (S,Z)-2-(((1-(2-aminothiazol-4-yl)-2-((2,2-dimethyl-d6-4-oxo-1-(sulfooxy)azetidin-3-yl)amino)-2-oxoethylidene)amino)oxy)acetic acid A cohort of three rats was IV dosed using 2 mg/kg cassette IV dosing. The cassette included 1 mg/kg of tigemonam and 1 mg/kg of gem-dimethyl d6 analog ((S,Z)-2-(((1-(2-aminothiazol-4-yl)-2-((2,2-dimethyl-d6-4-oxo-1-(sulfooxy)azetidin-3-yl)amino)-2-oxoethylidene)amino)oxy)acetic acid). Samples were withdrawn at various time points indicated below and processed using the following procedure. A 50 µL rat plasma sample was transferred to a well of a 96 well-plate, 20 µL of 0.1 ng/µL of Losartan (internal standard) in acetonitrile was added and 300 µL of acetonitrile/formic acid (100/2). The sample was then vortexed and centrifuged at 300 rpm for 5 minutes. Then 200 µL of the supernatant was mixed with 200 µL of double distilled water and was injected (5 µL) on a phenomex Polar-RP 80A column (75×2.0 mm), which was run at 30° C. at a flow rate of 600 µL/minute with a mobile phase A of acetonitrile/formic acid 100/0.02 and a mobile phase B of water/formic acid 100/0.02. The eluate was analyzed by LC/MS/MS (electrospray) to provide the following values of plasma concentration vs. time listed in Table 1, which were then plotted to yield the graph illustrated in FIG. 1.

TABLE 1

| Time (hours) | a (ng/mL) | b (ng/mL) | r = b − a | Ratio of b/a |
|---|---|---|---|---|
| 0.167 | 5262 | 5497 | 235 | 1.04 |
| 0.5 | 2030 | 2049 | 19 | 1.01 |
| 1 | 468 | 437 | −31 | .9 |
| 2 | 146 | 167 | 21 | 1.14 |
| 4 | 32 | 34 | 2 | 1.06 |
| 6 | 5 | 3 | −2 | .6 |
| 8 | 0 | 0 | 0 | |
| 24 | 0 | 0 | 0 | | a and b in Table 1 above refer to tigemonam and (S,Z)-2-((((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid, respectively. Each time point above represents a value obtained by averaging the measured plasma concentration of three rats. As can be seen from Table 1, the plasma levels of tigemonam (solid line in FIG. 1) and (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid (dashed line in FIG. 1) were almost identical. Deuteration of tigemonam thus appears to have no effect on IV bioavailability.

Figure 2:
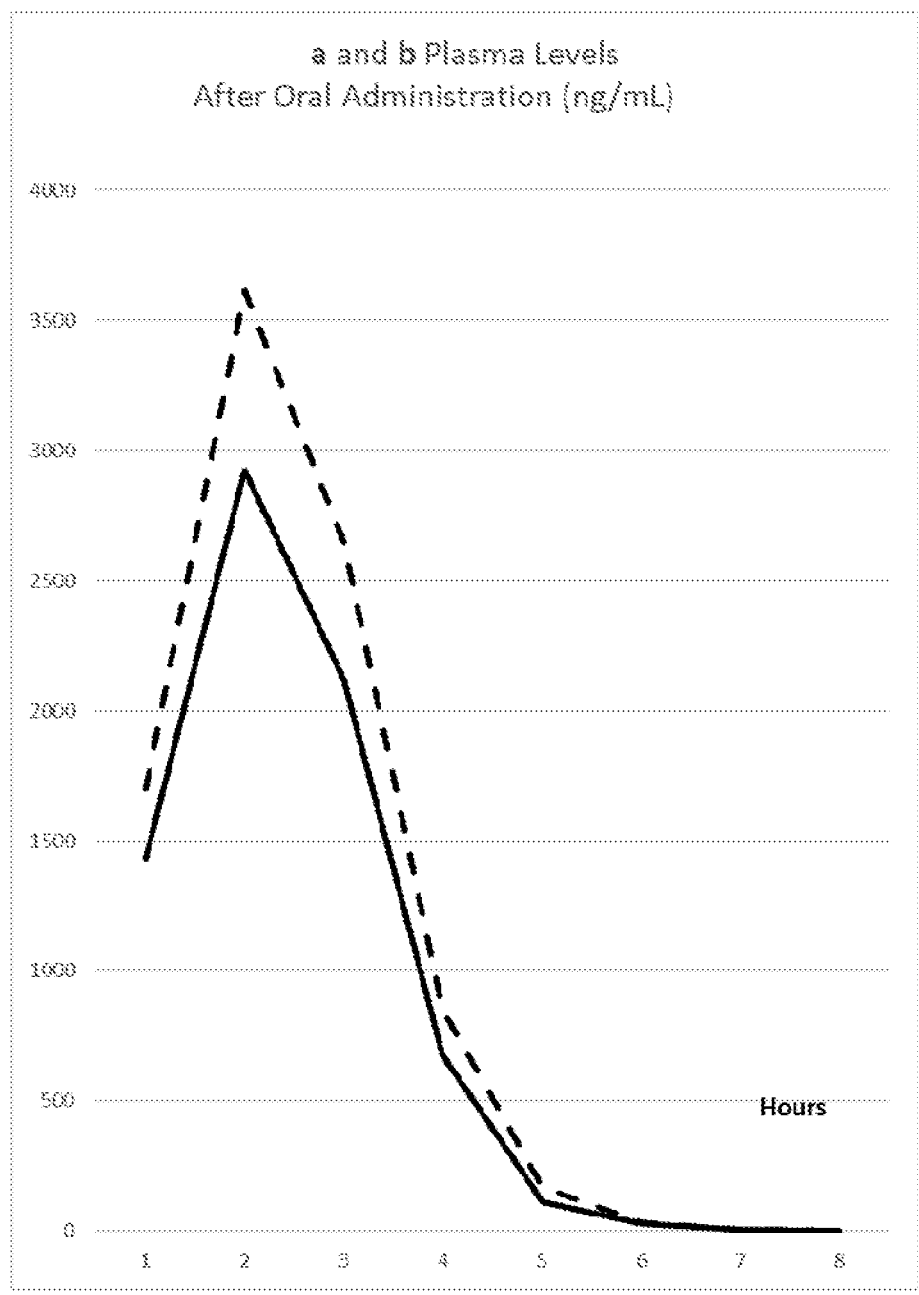
FIG. 2 is a graph which illustrates oral dosing of tigemonam (solid line) and (S,Z)-2-(((1-(2-aminothiazol-4-yl)-2-((2,2-dimethyl-$d_6$-4-oxo-1-(sulfooxy)azetidin-3-yl)amino)-2-oxoethylidene)amino)oxy)acetic acid (dashed line) in rats where the y axis is plasma concentration (ng/mL) and the x axis is time (hours).

Example 36: Oral Dosing of Tigemonam and (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid A cohort of three rats was orally dosed using 10 mg/kg cassette IV dosing. The cassette included 5 mg/kg of tigemonam and 5 mg/kg of gem-dimethyl d$_6$ analog ((S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid). Samples were withdrawn at various time points indicated below and processed using the following procedure. A 50 μL rat plasma sample was transferred to a well of a 96 well-plate, 20 μL of 0.1 ng/μL of Losartan (internal standard) in acetonitrile was added and 300 μL of acetonitrile/formic acid (100/2). The sample was then vortexed and centrifuged at 300 rpm for 5 minutes. Then 200 μL of the supernatant was mixed with 200 μL of double distilled water and was injected (5 μL) on a phenomex Polar-RP 80A column (75×2.0 mm), which was run at 30° C. at a flow rate of 600 μL/minute with a mobile phase A of acetonitrile/formic acid 100/0.02 and a mobile phase B of water/formic acid 100/0.02. The eluate was analyzed by LC/MS/MS (electrospray) to provide the following values of plasma concentration vs. time listed in Table 1, which were then plotted to yield the graph illustrated in FIG. 2.

TABLE 2

| Time (hours) | a (ng/mL) | b (ng/mL) | r = b − a | Ratio of b/a |
|---|---|---|---|---|
| 0.167 | 1434 | 1700 | 266 | 1.19 |
| 0.5 | 2923 | 3617 | 694 | 1.24 |
| 1 | 2121 | 2652 | 531 | 1.25 |
| 2 | 679 | 854 | 175 | 1.26 |
| 4 | 114 | 169 | 55 | 1.48 |
| C6 | 27 | 31 | 4 | 1.15 |
| 8 | 04 | 5 | 1 | 1.25 |
| 24 | 0 | 0 | 0 | | a and b in Table 1 above refer to tigemonam and (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid, respectively. Each time point above represents a value obtained by averaging the measured plasma concentration of three rats. As can be seen from Table 1 and FIG. 2, the plasma level of (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid (dashed line in FIG. 2) was at least about 20% greater than the plasma level of tigemonam (solid line in FIG. 2). The above results indicates that S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid is orally absorbed at an increased level when compared with tigemonam. Deuteration of tigemonam, thus appears to increase oral bioavailability of the antibiotic. Other compounds may also be tested in the above assay.

Example 37: Efficacy of (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid Alone or in Combination with a Carbapenem Antibiotic in a Mouse Thigh Model of K. Pneumoniae or E. Coli, Infection The following is an example of an animal assay which is used to demonstrate efficacy of compounds disclosed herein in treating infection with bacterial pathogens. Those of skill in the art will appreciate that variations in certain parameters may be made.

All animal experiments are performed under IACUC review with ethical committee clearance. Mice used in this study are specific pathogen free. Mice are allowed to acclimatize for 7 days and weighted 20-25 g at the start of the experiment. Mice are housed in sterile individual ventilated cages. The mice are exposed at all times to HEPA filtered sterile air. Mice have free access to food and water (sterile) and have sterile aspen chip bedding (is changed every 3-4 days or as is appropriate). A. Klebsiella pneumoniae isolate or *Escherichia coli* isolate resistant to antibiotics is used throughout the study.

In this study, 6 mice are used in each treatment group. Mice are rendered temporarily neutropenic by immunosuppression with cyclophosphamide at 150 mg/kg four days before infection and 100 mg/kg one day before infection by intraperitoneal injection. The immunosuppression regime leads to neutropenia starting 24 hours post administration which continues throughout the study. 24 hours post the second round of immunosuppression mice are infected with bacteria intramuscularly into both lateral thigh muscles using approximately 2.5×10 cfu/mouse thigh. Antibacterial treatment is initiated 2 hours post infection and is administered by gavage 2-3 times per 24 h. An aliquot of 4% CHD-FA stock solution as adjusted to pH 5 with 10 M sodium hydroxide solution is then diluted either 1:2 or 1:8 with 0.9% saline to give a dosing solution of 2% (200 mg/kg) and 0.5% (50 mg/kg) CHD-FA respectively. Twenty-four hours post infection, the clinical condition of all animals is assessed prior to them being humanely euthanized. Animal weight is determined before both thighs are removed and weighed individually. Individual thigh tissue samples are homogenized in ice cold sterile phosphate buffered saline. Thigh homogenates are then quantitatively cultured onto CLED agar and incubated at 37° C. for 24 hrs and colonies are counted daily. Results of CFU/gr and mortality are used to establish the potency of (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid vs comparator.

It is expected that animals treated with (S,Z)-2-(((1-(2-aminothiazol-4-yl)-2-((2,2-dimethyl-d$_6$-4-oxo-1-(sulfooxy)azetidin-3-yl)amino)-2-oxoethylidene)amino)oxy)acetic acid will have reduced CFU/gr and reduced mortality compared to untreated animals and animals treated with an equivalent amount of tigemonam.

All references, patents or applications, U.S. or foreign, cited in the application are hereby incorporated by reference as if written herein in their entireties. Where any inconsistencies arise, material literally disclosed herein controls. Such references are not admitted to be prior art relevant to analysis of novelty, obviousness, or inventive step.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula (III):

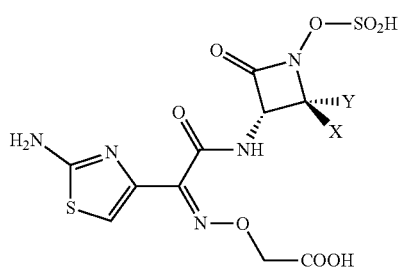

(III)

or a pharmaceutically acceptable salt, hydrate, or solvate thereof, wherein:

each of X and Y is independently selected from —CH₃ and —CD₃;

at least one of X and Y is —CD₃; and the level of deuterium enrichment at each position denoted D is at least 50%.

2. The compound of claim 1, having the structure:

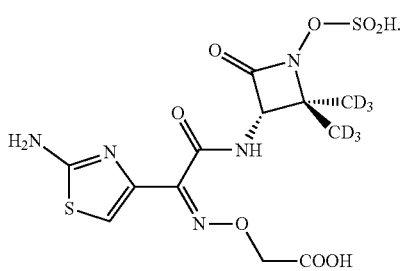

3. The compound of claim 1, having the structure:

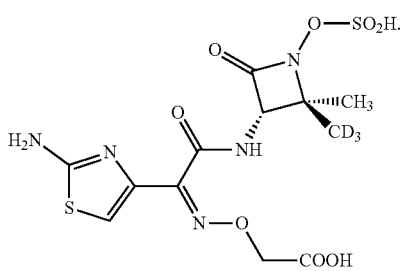

4. The compound of claim 1, having the structure:

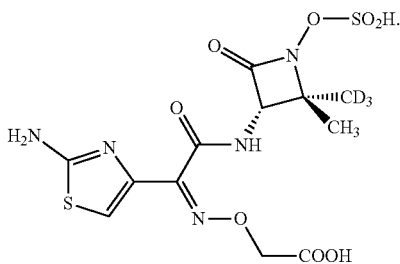

5. A pharmaceutical composition comprising the compound of claim 1, or a pharmaceutically acceptable salt, hydrate, or solvate thereof, and a pharmaceutically acceptable excipient.

6. The compound of claim 1, wherein the level of deuterium enrichment at each position denoted D is at least 70%.

7. A pharmaceutical composition comprising the compound of claim 6, or a pharmaceutically acceptable salt, hydrate, or solvate thereof, and a pharmaceutically acceptable excipient.

8. The compound of claim 1, wherein the level of deuterium enrichment at each position denoted D is at least 80%.

9. A pharmaceutical composition comprising the compound of claim 8, or a pharmaceutically acceptable salt, hydrate, or solvate thereof, and a pharmaceutically acceptable excipient.

10. The compound of claim 1, wherein the level of deuterium enrichment at each position denoted D is at least 90%.

11. A pharmaceutical composition comprising the compound of claim 10, or a pharmaceutically acceptable salt, hydrate, or solvate thereof, and a pharmaceutically acceptable excipient.

12. The compound of claim 1, wherein the level of deuterium enrichment at each position denoted D is at least 98%.

13. A pharmaceutical composition comprising the compound of claim 12, or a pharmaceutically acceptable salt, hydrate, or solvate thereof, and a pharmaceutically acceptable excipient.

14. A compound having the structure:

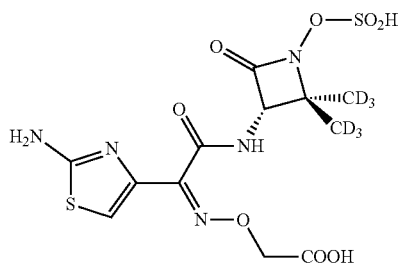

or a pharmaceutically acceptable salt, hydrate, or solvate thereof, wherein the level of deuterium enrichment at each position denoted D is at least 90%.

15. A pharmaceutical composition comprising the compound of claim 14, or a pharmaceutically acceptable salt, hydrate, or solvate thereof, and a pharmaceutically acceptable excipient.

16. A compound having the structure:

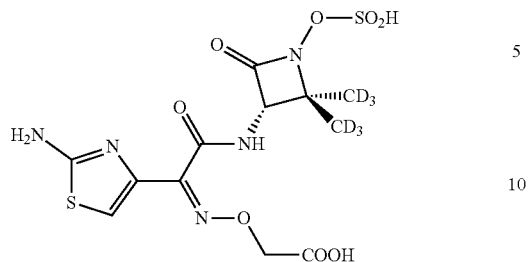

or a pharmaceutically acceptable salt, hydrate, or solvate thereof, wherein the level of deuterium enrichment at each position denoted D is at least 98%.

17. A pharmaceutical composition comprising the compound of claim 16, or a pharmaceutically acceptable salt, hydrate, or solvate thereof, and a pharmaceutically acceptable excipient.

18. A pharmaceutical composition comprising the compound of claim 3, or a pharmaceutically acceptable salt, hydrate, or solvate thereof, and a pharmaceutically acceptable excipient.

19. A pharmaceutical composition comprising the compound of claim 4, or a pharmaceutically acceptable salt, hydrate, or solvate thereof, and a pharmaceutically acceptable excipient.

* * * * *

UNITED STATES PATENT AND TRADEMARK OFFICE
CERTIFICATE OF CORRECTION

PATENT NO. : 10,047,077 B2
APPLICATION NO. : 15/486555
DATED : August 14, 2018
INVENTOR(S) : Eric Gordon It is certified that error appears in the above-identified patent and that said Letters Patent is hereby corrected as shown below:

In the Claims

Column 73, Line 12 (Claim 1), that reads "$SO_2H$" should read -- $SO_3H$ --.

Column 73, Line 38 (Claim 2), that reads "$SO_2H$." should read -- $SO_3H$. --.

Column 73, Line 56 (Claim 3), that reads "$SO_2H$." should read -- $SO_3H$. --.

Column 74, Line 4 (Claim 4), that reads "$SO_2H$." should read -- $SO_3H$. --.

Column 74, Line 49 (Claim 14), that reads "$SO_2H$" should read -- $SO_3H$ --.

Column 75, Line 4 (Claim 16), that reads "$SO_2H$" should read -- $SO_3H$ --.

Signed and Sealed this
Second Day of April, 2019

Andrei Iancu
*Director of the United States Patent and Trademark Office*